(12) United States Patent
Moorman et al.

(10) Patent No.: US 10,582,873 B2
(45) Date of Patent: Mar. 10, 2020

(54) ANALYSIS OF CARDIAC RHYTHM USING RR INTERVAL CHARACTERIZATION

(71) Applicant: University of Virginia Patent Foundation, Charlottesville, VA (US)

(72) Inventors: J. Randall Moorman, Keswick, VA (US); Douglas E. Lake, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 0 days.

(21) Appl. No.: 15/973,024

(22) Filed: May 7, 2018

(65) Prior Publication Data
US 2019/0038163 A1 Feb. 7, 2019

Related U.S. Application Data

(60) Continuation of application No. 14/615,038, filed on Feb. 5, 2015, now Pat. No. 9,962,101, which is a division of application No. 12/594,842, filed as application No. PCT/US2008/060021 on Apr. 11, 2008, now Pat. No. 8,983,584.

(60) Provisional application No. 60/998,664, filed on Oct. 12, 2007, provisional application No. 60/923,080, filed on Apr. 12, 2007.

(51) Int. Cl.
| | |
|---|---|
| A61B 5/0456 | (2006.01) |
| A61B 5/00 | (2006.01) |
| G06K 9/00 | (2006.01) |
| A61B 5/048 | (2006.01) |
| A61B 5/046 | (2006.01) |
| A61B 5/0452 | (2006.01) |
| A61N 1/39 | (2006.01) |
| G16H 50/20 | (2018.01) |

(52) U.S. Cl.
CPC ............ *A61B 5/0456* (2013.01); *A61B 5/046* (2013.01); *A61B 5/048* (2013.01); *A61B 5/412* (2013.01); *A61B 5/7242* (2013.01); *A61B 5/7264* (2013.01); *G06K 9/00523* (2013.01); *A61B 5/0452* (2013.01); *A61N 1/395* (2013.01); *G16H 50/20* (2018.01)

(58) Field of Classification Search
CPC .................................................... A61B 5/0452
USPC .............................. 600/508, 509, 518; 607/4
See application file for complete search history.

*Primary Examiner* — Nadia A Mahmood
(74) *Attorney, Agent, or Firm* — Buchanan Ingersoll & Rooney PC

(57) ABSTRACT

A method for analysis of cardiac rhythms, based on calculations of entropy and moments of interbeat intervals. An optimal determination of segments of data is provided that demonstrate statistical homogeneity, specifically with regard to moments and entropy. The invention also involves calculating moments and entropy on each segment with the goal of diagnosis of cardiac rhythm. More specifically, an absolute entropy measurement is calculated and provided as a continuous variable, providing dynamical information of fundamental importance in diagnosis and analysis. Through the present invention, standard histograms, thresholds, and categories can be avoided.

10 Claims, 17 Drawing Sheets

ANALYSIS OF CARDIAC RHYTHM USING RR INTERVAL CHARACTERIZATION

CROSS-REFERENCE TO RELATED APPLICATIONS

This application is a division of copending application Ser. No. 12/594,842 filed Oct. 6, 2009, which is a National Stage of PCT Application No. PCT/US08/60021 filed Apr. 11, 2008, which claims benefit under 35 U.S.C. § 119(e) to U.S. Provisional Patent Application Ser. No. 60/923,080 filed on Apr. 12, 2007 and Ser. No. 60/998,664, filed on Oct. 12, 2007, which are hereby incorporated by reference in their entireties.

STATEMENT REGARDING FEDERALLY SPONSORED RESEARCH OR DEVELOPMENT

This invention was not made in the course of federally sponsored research or development.

THE NAMES OF THE PARTIES TO A JOINT RESEARCH AGREEMENT

This invention was not made in the course of joint research agreement.

BACKGROUND OF THE INVENTION

The present invention relates generally to the field of cardiology and in particular to detection and analysis of cardiac function. There is a serious need for detection of normal and abnormal cardiac rhythms using heart rate (HR) or interbeat interval series.

Several common clinical scenarios call for identification of cardiac rhythm in ambulatory out-patients. For example, atrial fibrillation (AF) is a common arrhythmia that is often paroxysmal in nature. Decisions about its therapy are best informed by knowledge of the frequency, duration and severity of the arrhythmia. While implanted devices can record this information with great accuracy, non-invasive diagnostic devices for recording electrocardiographic (EKG) signals are constrained by the need for skin electrodes. Non-invasive devices for determining heart rate from the pulse rate are not in common use because of reduced confidence in detecting AF based on the heart rate series alone. Specifically, sinus rhythm with frequent ectopy is expected to share many time series features with AF, and thus be difficult to distinguish. In addition, many other transient cardiac arrhythmias cause short-lived symptoms but are currently difficult to diagnose on the basis of heart rate time series alone.

Thus a need exists for confident diagnosis of normal and abnormal cardiac rhythms from heart rate time series such as would be provided by non-invasive devices that do not use a conventional EKG signal. Since a common and high-profile example of an abnormal cardiac rhythm is atrial fibrillation, its detection from heart rate time series alone is an object of the present invention.

Atrial fibrillation is an increasingly common disorder of cardiac rhythm in which the atria depolarize at exceedingly fast rates. Even with normal function of the atrioventricular (AV) node, which serves as the sole electrical connection between the atria and the ventricles and filters the high frequency of atrial impulses, atrial fibrillation can result in heart rates as high as 160 to 180 beats per minute. While these fast rates, along with the lack of atrial contractile function, may or may not cause symptoms, atrial fibrillation carries with it the risk of stroke because the lack of concerted atrial contraction allows blood clots to form. Thus the major emphases in treatment are conversion to normal sinus rhythm (NSR), control of heart rates, and anticoagulation to reduce the risk of stroke.

Patients with severe heart disease are at increased risk of ventricular tachycardia (VT) or fibrillation, and implantable cardioverter-defibrillator (ICD) devices are recommended to reduce the incidence of sudden cardiac death. ICDs are small battery-powered electrical impulse generators which are implanted in at-risk patients and are programmed to detect cardiac arrhythmia and correct it by delivering a jolt of electricity to the heart muscle. These patients are also at high risk of atrial fibrillation leading to inappropriate ICD shocks. While dual chamber devices allow better AF detection because the atrial electrical activity is known, single lead ICDs must rely entirely on the RR interval time series. There is a need to improve detection of AF in short records to reduce inappropriate ICD shocks.

The current management paradigm for patients with atrial fibrillation emphasizes anticoagulation and both heart rate control and attempts to convert to normal sinus rhythm (NSR). This is based on the findings of randomized clinical trials that showed no morbidity or mortality advantage to either rhythm control or rate control strategies as long as anticoagulation was maintained. Some principles that dominate the current practice are: anticoagulation for life once even a single paroxysm of AF has been detected in patients at risk for stroke; higher doses of AV nodal-blocking drugs to lower average heart rates, and more frequent AV junction ablation coupled with permanent electronic cardiac pacing; and cardioversion, anti-arrhythmic drugs and, if they fail, left atrial catheter ablation procedures to restore and maintain sinus rhythm.

Decisions about these therapeutic options are best made if there is accurate estimation of the proportion of time spent in AF, or the "AF burden." Many patients with AF are elderly, and in some there is a substantial risk of anticoagulation because of the propensity to fall. If indeed an episode of AF were truly never to recur, then the risk of anticoagulation after a few months could legitimately be avoided. There is a need, therefore, for a continuous monitoring strategy to determine the need for continued anticoagulation in patients thought to be free of AF.

Many patients with AF are unaware of persistently fast ventricular rates that would lead the physician to alter medications or to consider AV junction ablation therapy in conjunction with electronic ventricular pacing. This also demonstrates a need for a continuous monitoring strategy that reports descriptive statistics of the heart rate during AF.

Moreover, patients for whom rhythm control is attempted require continuous monitoring to determine the success of the therapy, and the need for further therapies if AF recurs.

Detection of AF can be accomplished with very high degrees of accuracy, if an intra-atrial cardiac electrogram from an implanted pacing lead or a conventional EKG signal from skin electrodes are available. Neither is as non-obtrusive as a device that records the time from one arterial pulse waveform to the next, but such a non-invasive device can provide only the heart rate time series with no information about cardiac electrical activity. Thus an algorithm and computer method for detecting AF in a heart rate or pulse rate series is a desirable goal.

Tateno and Glass developed a measure based on the reasoning that distinctive differences between AF and sinus (or other) rhythms lay in the degree of overall variability.

[See: K. Tateno and L. Glass, "Automatic detection of atrial fibrillation using the coefficient of variation and density histograms of RR and ΔRR intervals," Med Biol Eng Comput vol. 39, 664-671, 2001.]

Tateno and Glass used the canonical MIT-BIH Holter databases (www.physionet.org) to develop empirical cumulative distribution functions (ECDFs) of heartbeat interval and heart rates, and to test the hypothesis that a new data set belongs to the AF group. The resulting algorithm, which was based on 90% of the data sets, had diagnostic performance in the remaining 10%, with Receiver Operating Characteristic (ROC) area of 0.98, and sensitivity and specificity over 95% at some cut-offs.

Generally, there are some potential barriers to widespread implementation of the Tateno and Glass approach:

First, the data were collected from a non-random sample of 23 AF patients in the early 1980's when medical practices were different with regard to heart rate-controlling (HR-controlling) drugs and anti-congestive heart failure drugs. The average heart rate in the MIT-BIH Atrial Fibrillation Database is 96 beats per minute, compared to 81 beats per minute in the contemporary University of Virginia Holter Database.

Second, much rests on histograms of intervals occurring within 30-minute blocks that are arbitrarily segregated by the mean heart rate during the 30 minutes. This approach is vulnerable to large changes in results based on small differences in heart rates. Moreover, some ECDFs represent many more patients and data points than others. Choosing histogram boundaries so that each represents the same proportion of the entire database has appeal, but still suffers from inescapable problems when such bright cut-offs are employed.

Third, episodes of AF lasting less than 30 minutes might be missed altogether, if surrounded by very regular rhythms.

Fourth, the MIT-BIH arrhythmia database that was used for testing is relatively small.

Fifth, in the Tateno and Glass approach there is no analysis of the dynamics (i.e., the order) of RR intervals. This is an especially important distinction between the Tateno and Glass approach and the present invention.

With respect to the detection of atrial fibrillation from interbeat intervals, the Tateno and Glass method employs a Kolmogorov-Smirnov (KS) test of ECDFs of observed sets of ΔRR intervals (the difference between one RR interval and the next) versus empirical histograms of ΔRR intervals during atrial fibrillation (AF) obtained from MIT-BIH Atrial Fibrillation Database. The fundamental measurement is the largest distance, also called the KS distance, between ECDFs of observed data and a template data set. Large distances suggest that the data sets represent different cardiac rhythms. The KS distance method of Tateno and Glass is designed to distinguish AF from normal sinus rhythm (NSR) and from other arrhythmias such as paced rhythm, ventricular bigeminy and trigeminy, and others. Formally, the parameter calculated is the probability that the observed intervals arise from AF, thus small p-values (PV) provide evidence that data is not AF. Tateno and Glass suggest a cutoff of PV>0.01 as a diagnostic criterion for AF.

The 16 ECDFs of ΔRR intervals during AF are based on 10,062 non-overlapping 50 point AF episodes segregated by ranges of the mean RR interval distributed as shown in Table 1.

TABLE 1

| Mean RR | Segments |
|---|---|
| 350-399 | 38 |
| 400-449 | 325 |
| 450-499 | 548 |
| 500-549 | 1179 |
| 550-599 | 2114 |
| 600-649 | 1954 |
| 650-699 | 1256 |
| 700-749 | 913 |
| 750-799 | 386 |
| 800-849 | 342 |
| 850-899 | 256 |
| 900-949 | 331 |
| 950-999 | 265 |
| 1000-1049 | 124 |
| 1050-1099 | 24 |
| 1100-1149 | 7 |

There are appealing features of this method. There is nonparametric characterization of ΔRR densities; the mean RR interval is incorporated into the analysis; and it distinguishes AF from normal sinus rhythm (NSR) and from other arrhythmias in the MIT-BIH arrhythmia database.

However, the current art presents further limitations, disadvantages, and problems, in addition to the general limitations noted above.

First, the mean RR interval is not included as continuous variable, but rather in ranges. It is an object of the present invention to address the need for a new method, which utilizes the mean RR interval as a continuous variable.

Second, the empirical cumulative distribution function (ECDF) analysis is not dependent at all on non-AF rhythms. It is an object of the present invention to address the need for a new method wherein the ECDF analysis is dependent on non-AF rhythms.

Third, the analysis requires a large amount of histogram data (>500,000 data points) for implementation. It is an object of the present invention to address the need for a new method, which requires significantly less histogram data.

Fourth, the histograms for low (<400) and high (>1049) mean RR intervals are based on very few segments. It is an object of the present invention to address the need for a new method, which avoids this limitation.

Fifth, there are no histograms for extremely high (>1150) mean RR intervals. It is an object of the present invention to address the need for a new method, which avoids this limitation.

Sixth, the data are not independent, invalidating the theoretical p-value calculation. It is an object of the present invention to address the need for a new method, which utilizes independent data.

The long-felt need for a new method that addresses the limitations, disadvantages, and problems, discussed above, is evidenced by the many databases available for development and testing of new AF detection algorithms. Several databases have been used during the development and testing of the present invention.

The MIT-BIH Atrial Fibrillation (AF) Database, which consists of 10-hour recordings from 23 patients with AF. Each beat has been manually annotated as to its rhythm. In all, there are 299 segments of AF lasting a total of 91.59 hours (40%) and 510,293 beats. The database can be divided into 21,734 non-overlapping 50-point records with following distribution: AF 8320, NSR 12171, other 735 and mixed 508. For modeling of binary outcomes, the database can be considered as 8824 50-point records with any AF and 12,910 with no AF.

The MIT-BIH Arrhythmia (ARH) Database consists of two parts (100 series and 200 series) with 30-minute recordings (1500 to 3400 beats). The 100 series contains 23 subjects (48244 total beats) with no AF, but some other abnormal rhythms (7394 beats). The 200 series contains 25 subjects (64394 total beats) with 8 subjects with AF (12402 beats, 11%); other abnormal rhythms also present (13091 beats). The database can be divided into 2227 non-overlapping 50-point records with 289 (13%) having any AF. The overall distribution was AF 187, NSR 1351, other 255, and mixed 434. The development of new methods to detect atrial fibrillation has been limited, because the current go/no-go decision for developing new AF detection algorithms rests on analysis of the ARH database, which contains only about 2 hours of AF in 8 patients from more than 20 years ago.

Results obtained in the MIT-BIH databases may not hold up in widespread use because of their small sizes and highly selective nature. Accordingly, a more real-world data set of complete RR interval time series from consecutive 24-hour Holter monitor recordings has been analyzed.

The University of Virginia Holter Database consists of 426 consecutive 24-hour recordings from the Heart Station beginning in October, 2005. 206 are from males, and the median age is 58 years (10th percentile 23 years, 90th percentile 80 years). 76 (18%) gave "atrial fibrillation", "atrial fibrillation/flutter", or "afib-palpitations" as the reason for the test.

The dynamics of cardiac rhythms can be quantified by entropy and entropy rate under the framework of continuous random variables and stochastic processes [See C. E. Shannon, "A Mathematical Theory of Communication", Bell System Technical Journal, vol. 27, pp. 379-423 & 623-656, July & October, 1948].

Approximate entropy (ApEn) was introduced in 1991 as a measure that could be applied to both correlated random and noisy deterministic processes with motivation drawn from the fields of nonlinear dynamics and chaos theory [See: S. Pincus, "Approximate entropy as a measure of system complexity," Proc. Natl. Acad. Sci., vol. 88, pp. 2297-2301, 1991.]. There are limitations and possible pitfalls in the implementation and interpretation of ApEn, especially with the need to detect cardiac rhythms in relatively short data records.

Sample entropy (SampEn) is an alternative measure with better statistical properties and has successfully been utilized on neonatal heart rate data (HR data) to aid in the prediction of sepsis [See J. Richman and J. Moorman, "Physiological time series analysis using approximate entropy and sample entropy," Amer J Physiol, vol. 278, pp. H2039-H2049, 2000; and D. Lake, J. Richman, M. Griffin, and J. Moorman, "Sample entropy analysis of neonatal heart rate variability," Amer J Physiol, vol. 283, pp. R789-R797, 2002.]. See also U.S. Pat. No. 6,804,551 to Griffin et al. issued Oct. 12, 2004 and assigned to the same assignee herein. The '551 patent is incorporated herein by reference in its entirety.

SampEn has also been used as part of the promising new multiscale entropy (MSE) analysis technique to better discriminate adult HR data among normal, atrial fibrillation, and congestive heart failure patients [See: M. Costa, A. Goldberger, and C. Peng, "Multiscale entropy analysis of complex physiologic time series," Phys. Rev. Lett., vol. 89, no. 6, p. 068102, 2002.]. For purposes of comparison, this work is termed the deterministic approach to measuring complexity and order in heart rate variability.

Standard error estimates aid in evaluating the adequacy of the selected matching tolerance r which can be especially crucial for short records. An expression for approximating the variance of sample entropy was presented in D. Lake, J. Richman, M. Griffin, and J. Moorman, "Sample entropy analysis of neonatal heart rate variability," Amer J Physiol, vol. 283, pp. R789-R797, 2002, and used in selecting optimal values of m and r. Exploiting the special U-statistic structure of SampEn, this estimate has recently been improved upon and asymptotic normality established [See J. Richman, "Sample entropy statistics," Ph.D. dissertation, University of Alabama Birmingham, 2004]. Estimating the standard error for Apen and other Renyi entropy rate estimates has proved to be more complicated because of the dependency of the random process and the nonlinearities in the calculations.

With deterministic approaches the values of m and r are fixed for all the analysis (sometimes signal length is also constant). This is done to enable comparison of a wider variety of processes, but has several disadvantages. The choices of m and r vary from study to study and comparison of results is not always possible. Methods to optimally choose these parameters have been studied and this process has been a part of developing entropy measures for detecting atrial fibrillation [See: D. Lake, J. Richman, M. Griffin, and J. Moorman, "Sample entropy analysis of neonatal heart rate variability," Amer J Physiol, vol. 283, pp. R789-R797, 2002.].

Current implanted devices employ a "stability" algorithm based on the variability amongst a small number of interbeat or RR intervals, and "unstable" rhythms are interpreted as AF. The reasoning is that the most distinctive difference between AF and other rhythms lies in the degree of variability.

BRIEF SUMMARY OF THE INVENTION

An aspect of various embodiments of the present invention system, computer method (and related computer, computer system, and/or computer processor) and computer program product provides for automated classification of cardiac rhythm, atrial fibrillation in particular, based only on the times between heart beats. In part, an algorithm or computer method, which is based on novel entropy measures, can be used as a standalone diagnostic test for atrial fibrillation or as a component of multivariable diagnostic algorithms. The novel entropy measures are called, coefficient of sample entropy (COSEn). According to the present invention, the order of the heartbeat intervals as measured by COSEn has diagnostic importance not provided in traditional tests for atrial fibrillation that are based on the heart rate and the degree of variability.

The diagnostic performance, which is robust for series as short as 12 beats, is similar in the canonical MIT-BIH databases to the standard method developed by Tateno and Glass.

Various preferred embodiments of the present invention implement the coefficient of sample entropy (COSEn) for detection of AF in short records. COSEn is a measure of regularity that is optimized for detection of AF in heart rate time series. COSEn incorporates sample entropy, the conditional probability that two heart rate sequences of length m, having matched within a specified tolerance, will also match at the next point. The further modifications allow for different values of the tolerance allowed, and for the mean heart rate.

Implementation of COSEn as an AF detector has several advantages over existing methods. For example, COSEn exploits information in the ordering of heart beat intervals, a key difference between AF and other rhythms. COSEn requires as few as 12 beats for accurate AF detection. COSEn is independent of heart rate—that is, works well at fast rates. COSEn adds statistically significant independent information to variability measures.

As an example, FIG. 1 shows the 24-hour heartbeat time series recorded by a Holter monitor at the University of Virginia. Beats labeled as normal sinus rhythm are in blue, and beats labeled as atrial fibrillation are in green. Note that the y-axis is RR interval, and AF is characterized by faster rates (shorter intervals) as well as increased variability. The purple line at the bottom is the COSEn, calculated every 50 beats. The arrow marks a threshold above which the beat would be labeled as atrial fibrillation. There is good agreement between this single statistical measure and the time series appearance, affirming the utility of the new measure as a diagnostic test for atrial fibrillation. There is good agreement between the data labels and the value of COSEn, with values above the threshold corresponding to epochs of AF.

The new algorithm and computer method, according to various embodiments of the present invention, is designed for accurate detection of atrial fibrillation in implanted devices in which atrial activity is not measured, such as single lead implantable cardioverter-defibrillators, and in prolonged monitoring such as mobile cardiac outpatient telemetry.

A further aspect of various embodiments of the present invention provides a new computer methodology, system and computer program product of multivariate statistical models that employ entropy measures. This aspect answers some of the limitations and deficiencies discussed above with regard to previous methods. For example, in an embodiment of a method, preferably a computer method, according to the present invention:

1) RR intervals are characterized by their dynamics, taking into account the order of the data points;

2) the novel dynamic parameters include differential quadratic Renyi entropy rate measured using the SampEn algorithm, which is well-suited for missing points and small records;

3) both normalized sample entropy, denoted by SE, non-normalized sample entropy, denoted by Q, and the coefficient of sample entropy (COSEn) are taken into account; and 4) these new dynamical measures are combined with density parameters such as mean, standard deviation and coefficient of variation (CV) measured using histogram summary statistics—importantly, in the method according to various embodiments of the present invention, these parameters are considered as continuous values, not ranges.

In a further aspect of the present invention, method, system, and computer program product, atrial fibrillation is detected using a multivariable analysis such as a logistic regression model trained to predict the probability that a given segment of RR intervals is from a patient in atrial fibrillation. Other multivariable methods such as neural networks, nearest-neighbor analyses and others would also be suitable.

Results from the method of the present invention method have been compared to the KS distance method of Tateno and Glass in the canonical and publicly available MIT-BIH AF Database. Representative predictive models perform well in detecting AF, as assayed by receiver-operating characteristics (ROC) areas as shown later. Note that the method of various embodiments of the present invention only requires a few coefficients for implementation regardless of number of AF patients used to train model. This is more efficient than repeated comparisons to multiple histograms, as is called for in the KS distance method of Tateno and Glass.

Various embodiments of the present invention involve classifying Cardiac Rhythms using Moments and Entropy Rates of RR intervals.

The various algorithms used in embodiments of the present invention overcome the potential problems of the prior art of classifying cardiac rhythm and detecting AF. Various aspects of the present invention may be based on several fundamental differences between AF and other rhythms. The first is the variability itself—AF has more—and the second is the order of the heartbeat intervals—AF has less. A third difference is that the blood pressure level and variability are altered. Thus, the measurements used to classify cardiac rhythms fall into two basic categories 1) estimates of the moments of RR intervals and transformed RR intervals 2) estimates of the entropy rate of the heart beat and transformed heart beat series to characterize the heart rate dynamics.

The first category includes measurements that are associated with established statistical methods, such as the coefficient of variation and histograms of the RR intervals, but also includes the novel moments after the logarithmic or the unit mean transformation of heart rate interbeat intervals. The second category includes the family of Renyi entropy (or q-entropy) rates as described in Lake D E, Renyi entropy measures of heart rate Gaussianity. IEEE Transactions on Biomedical Engineering, Volume 53(1):21-27, 2006.

The variance and bias of entropy estimates becomes a significant issue for short records, and an appropriate member of the family to emphasize is differential quadratic entropy rates (q=2) which is denoted by Q and calculated using the SampEn algorithm with optimized values of the parameters m, and r (See J. Richman and J. Moorman, "Physiological time series analysis using approximate entropy and sample entropy," Amer J Physiol, vol. 278, pp. H2039-H2049, 2000. and D. Lake, J. Richman, M. Griffin, and J. Moorman, "Sample entropy analysis of neonatal heart rate variability," Amer J Physiol, vol. 283, pp. R789-R797, 2002.).

One member of these families of measurements proves to be particularly strong in discriminating atrial fibrillation from normal sinus rhythm and other arrhythmias and deserves being treated as a new third category, which we term coefficient of entropy (COE) measures. The coefficient of entropy is a calculation of an entropy rate (or entropy) of an RR interval series after it has been unit mean normalized (dividing each observation by the mean of the series). This is analogous to the coefficient of variation, which is the standard deviation after normalization by the mean. In practice, the calculation of the coefficient of entropy is accomplished by subtracting the natural logarithm of the mean from the original entropy calculation. The coefficient of entropy calculated for Q in this way is especially effective and we give it the name coefficient of sample entropy or COSEn for short and denote it by Q*. A section describing the calculation of the new measure COSEn in more detail appears below.

An aspect of various embodiments of the present invention provides a new computer method, system and computer program product for analysis of cardiac rhythm based on calculations of entropy and moments of interbeat intervals.

A first part of an embodiment of the present invention provides an optimal determination of segments of data that are arbitrarily similar with regard to moments and entropy. The second part of the new invention consists of further calculations of moments and entropy that are performed on each segment with the goal of diagnosis of cardiac rhythm.

Some exemplary advantages associated with various embodiments of the present invention over current art include, but are not limited to, the following: (1) determination of optimal segmentation of the data record, as opposed to fixed record lengths, (2) consideration of the order of intervals, wherein important diagnostic information has been neglected, (3) simplicity of computation, (4) avoidance of comparisons to standards, and (5) a single method producing a continuous measurement, rather than numerous methods relying on thresholds and categories.

These advantages provide solutions to problems inherent to the current art of comparing histograms of interbeat interval differences to standard histograms, which (1) are constrained by fixed record lengths, which may contain more than one rhythm, (2) do not utilize dynamical information from the order of intervals, (3) require storage of standard histogram data, (4) require consensus standards from large numbers of well-characterized patients, and (5) run the risk of large changes in results based on very small differences in data that are near thresholds of categories.

Embodiments of the present invention involve using entropy and moment calculations to determine optimal segmentation of the data record for rhythm classification.

Embodiments of the present invention avoid using standard histograms, thresholds, and categories.

Embodiments of the present invention involve using an entropy calculation to make use of dynamical information of cardiac rhythm. Dynamical information of cardiac rhythm is of fundamental importance in diagnosis and analysis. Using dynamical information of cardiac rhythm provides improved results over methods that rely only on distributions of interbeat intervals without extracting information about the order in which they appear.

DETAILED DESCRIPTION OF THE INVENTION

Figure 1:
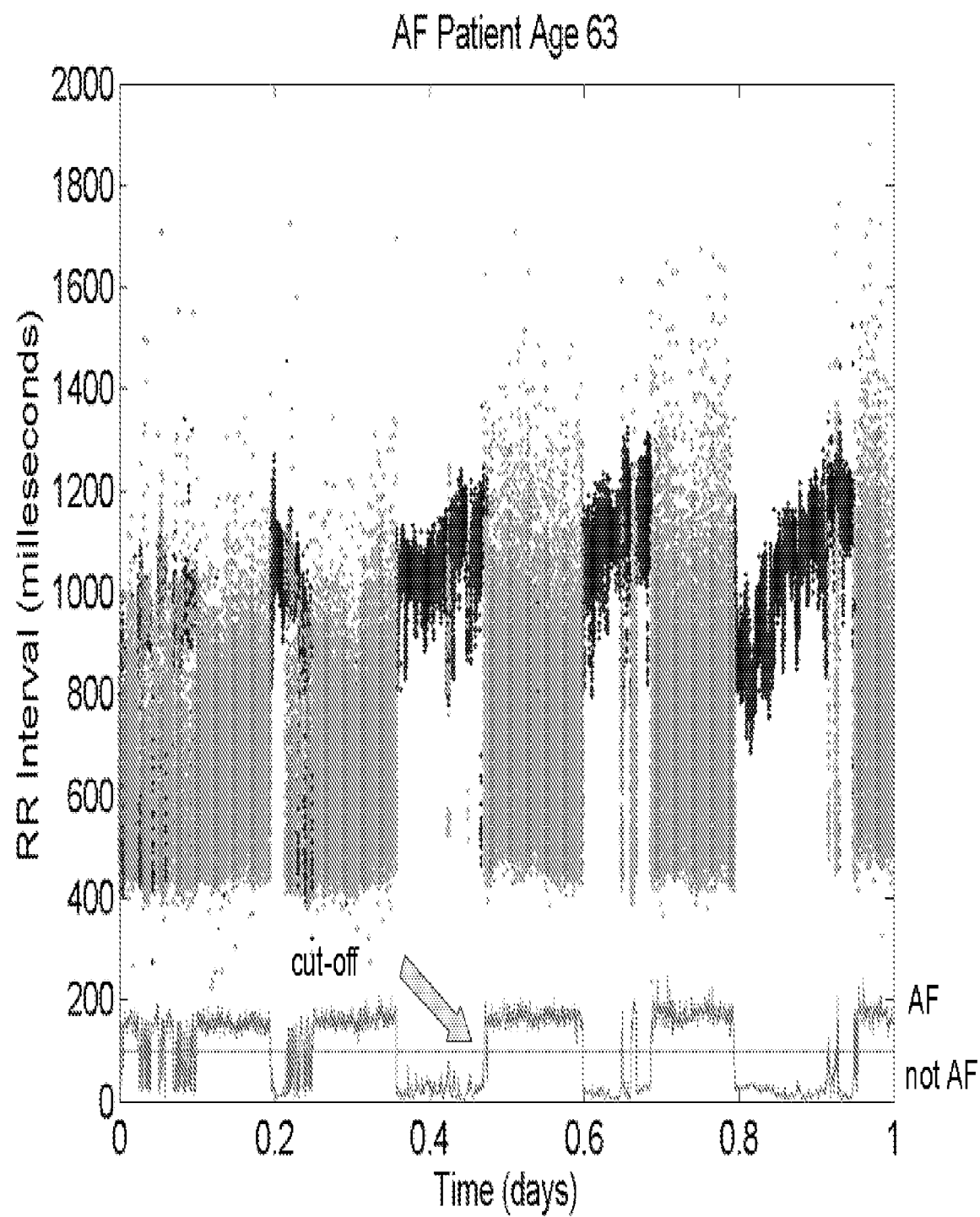
FIG. 1 shows a 24-hour Holter recording from a patient in NSR with paroxysmal AF, demonstrated by blue and green RR interval data points.

Various embodiments of the present invention utilize entropy and entropy rate for analyzing rhythms, preferably cardiac rhythms.

The dynamics of cardiac rhythms can be quantified by entropy and entropy rate under the framework of continuous random variables and stochastic processes. The entropy of a continuous random variable X with density $f$ is $$H(X)=E[-\log(f(X))]=\int_{-\infty}^{\infty}-\log(f(x))f(x)dx$$

If X has variance $\sigma^2$, then Y=X/σ has variance 1 and density $\sigma f(\sigma y)$. So the entropy of Y is related to the entropy of X by $$H(Y)=\int_{-\infty}^{\infty}-\log(\sigma f(\sigma y))\sigma f(\sigma y)dy=H(X)-\log(\sigma)$$

which shows that reduced entropy is indicative of reduced variance or increased uncertainty.

Another important property of entropy is provided by the inequality $$H(X) \le \frac{1}{2}(\log(2\pi e) + \log(\sigma^2)) = H(\sigma Z)$$

where Z is a standard Gaussian random variable. This result shows that the Gaussian distribution has maximum entropy among all random variables with the same variance. Thus, an estimate of entropy that is substantially lower than this upper bound for a random sample (with sample variance used as an estimate of $\sigma^2$) provides evidence that the underlying distribution is not Gaussian. This type of distribution is a characteristic of some cardiac arrhythmias, such as bigeminy and trigeminy, that are multimodal and is another reason entropy is important for this application.

Letting X denote the random sequence $X_1, X_2, X_3, \ldots$, the entropy rate of X is defined as $$H(X) = \lim_{n\to\infty} \frac{H(X_1, X_2, \ldots, X_n)}{n}$$

where the joint entropy of in random variables $X_1, X_2, \ldots, X_m$ is defined as $$H(X_1, X_2, \ldots, X_m)=E[-\log(f(X_1, X_2, \ldots, X_m))]$$

and $f$ is the joint probability density function $f$. For stationary processes, an equivalent definition is $$H(X) = \lim_{m \to \infty} H_m(X) = \lim_{m \to \infty} H(X_{m+1} | X_1, X_2, \ldots, X_m)$$

so entropy rate is the entropy of the conditional distribution of the present observation given the past. The entropy rate for i.i.d. sequences reduces to the entropy of the common distribution.

Estimating the entropy rate for sequences depends on estimates of its densities of order m. Let $X_1, X_2, \ldots, X_n$ denote a stationary random sequence and $X_i(m)$ denote the template consisting of the m×1 vector $(X_{i-m+1}, X_{i-m}, \ldots, X_i)^T$. For notational simplicity, let $X_n = X_n(n)$ denote the whole sequence and $X = X_\infty$ denote the limiting infinite sequence. The sequence $X_m(m), X_{m+1}(m), \ldots, X_n(m)$ is not independent, but many methods developed to analyze independent vector data are applicable. In particular, the $m^{th}$-order probability density function of the sequence, $f$, and entropy $$E[-\log(f(X_1, X_2, \ldots, X_m))]$$

can still be estimated empirically. These are the fundamental calculations in ApEn and SampEn.

The log-likelihood of a random sequence $X_n$ can be written as $$\log L(X_n) = \log(f(X_1, X_2, \ldots, X_n))$$
$$= \sum_{i=1}^{n} \log(f(X_i | X_1, X_2, \ldots, X_{i-1}))$$

and the Shannon-McMillan-Breiman theorem [13] states that for stationary ergodic processes the entropy rate of X is related to the log-likelihood function by $$H(X) = \lim_{n \to \infty} \frac{1}{n} E[-\log L(X_n)]$$

where the convergence is with probability 1. As part of our invention, we use the term model-based entropy to indicate the estimate $$\hat{H} = H(X_n, \hat{\theta}) = -\frac{1}{n} \log L(X_n; \hat{\theta})$$

obtained by modeling X by a parameter θ estimated by the MLE $\hat{\theta}$. In the current application, X represents a sequence from a particular cardiac arrhythmia that follows a particular parametric model.

All traditional time-series models, such as autoregressive (AR) models, could be applied to cardiac arrhythmias under this approach. In addition to increased flexibility, there is an important connection between this and the current art. In particular, ApEn corresponds to model-based entropy where the parameters are the transition probabilities of a Markov chain of order m and they are estimated empirically.

According to preferred embodiments of the present invention, the detection of cardiac rhythms is based on a series of the interbeat or RR intervals, which arise from a complex combination of both deterministic and stochastic physiological processes.

A complementary approach included as part of this invention is to consider HR data sufficiently stochastic to model it as a random process. We have developed stochastic Renyi entropy rate measures that can be reliably estimated with known statistical properties.

Embodiments of the present invention involve consideration of the standard error of Renyi Entropy Rate Estimates.

It is important to know the standard error of entropy rate estimates in order to be able to assess significant differences between cardiac rhythms and conduct meaningful statistical inference.

To demonstrate the novel approach of this invention, consider estimating the entropy rate. Letting $\hat{H}_i = -\log(\hat{f}_i)$, the entropy rate estimate $\hat{H}_i$ is the mean of the sample $\hat{H}_1, \hat{H}_2, \ldots \hat{\ldots}$ which can be viewed as an observation from a stationary random process. Let $\hat{\sigma}^2$ denote the sample variance and $\hat{c}_k$ denote the sample correlation coefficient at lag k calculated using a divisor of $n_k = n-k$, the number of pairs of observations at lag k. Then the variance of the entropy estimate can be estimated by $$\sigma_{\hat{H}}^2 = \frac{\hat{\sigma}^2}{n}\left(1 + 2\sum_{k=1}^{K} n_k \hat{c}_k\right)$$

and K is the maximum lag at which the random process has significant correlation. The optimal determination of K is application dependent, but our invention currently uses a conservative approach of selecting the value that results in the largest variance.

This same general approach can be used to estimate the standard errors of conditional Renyi entropy rates. In this case, the result comes from analyzing the sequence $\hat{f}_1^{q-1}, \hat{f}_2^{q-1}, \ldots \hat{\ldots}$. An estimate $\hat{\sigma}_q^2$ of the variance can be calculated using the same expression as above with the sample variance and correlation coefficients calculated from this sequence. Then, the standard error of the entropy estimated is approximated by $$\sigma_{\hat{R}_q^*} = \frac{\hat{\sigma}_q}{|q-1|\hat{\mu}_q}$$

where $\hat{\mu}_q$ is the sample mean of the sequence.

The stochastic Renyi entropy rate measures according to the present invention can be interpreted in ways that are analogous to the deterministic concepts of complexity and order, and is not fundamentally different. While developed under a stochastic framework, the algorithms are easily modified to compute deterministic approach measures that include both ApEn and SampEn. There are several basic differences between the stochastic approach and the deterministic approaches, and each has potential application to the detection of cardiac rhythms.

First, the deterministic approach involves calculating probabilities while the stochastic approach calculates probability densities. The probabilities involve matches of templates of length m within a tolerance r and converting them to densities by dividing by the volume of the matching region, which is $(2r)^m$. This simply reduces to adding a factor of $\log(2r)$ to ApEn or SampEn. The stochastic approach becomes viable when the values converge as r tends to 0 and the deterministic approach is diverging.

Various embodiments of the present invention use both fixed value of r=50 msec as well as r=f(S.D.). With fixed values, there is always the possibility of encountering data that results in highly inaccurate entropy estimates, so included in our invention is the continued development of absolute entropy measures independent of m and r that are statistically reliable and allows for comparison between a wide range of HR data sets.

With the stochastic approach, the goal is to estimate the theoretical limiting value as r goes to zero. The value of r for estimation does not need to be fixed and can be optimized for each signal. In addition, for longer records embodiments of the present invention also include in the invention the option of not fixing m and instead estimating the theoretical limiting value as m tends to infinity. One advantage of this general philosophy is that tolerances and template lengths can be selected individually for each signal to ensure accurate estimates. Even if it is advantageous or necessary to compare signals at the same value of r, our invention allows the flexibility of using different tolerances for estimation and applying a correction factor.

This idea is particularly important in the current setting of estimating entropies of quantized RR intervals obtained from coarsely sampled EKG waveforms. Another issue commonly encountered in analyzing RR interval data is that of quantization at the resolution of the sampling rate of the EKG signal. This means that all tolerances r within the resolution will result in the exact same matches and the issue becomes what value r should be used to calculate the entropy rate. The proper choice is to pick the value midway between the quantized values of r. For example, the EKG signal was sampled at 250 HZ in the AF Database and the RR intervals are at a resolution of 4 milliseconds. In this case, all tolerances between, say, 12 and 16 milliseconds would be considered 14 for the log(2r) term. This continuity correction can be nontrivial when tolerances are close to the resolution of the data. This is a novel aspect of our invention that optimizes the accuracy and discriminating capability of the entropy measures.

Various embodiments of the present invention relate to calculating Coefficient of Sample Entropy (COSEn), and preferably to AF detection using COSEn, in short records.

Figure 5:
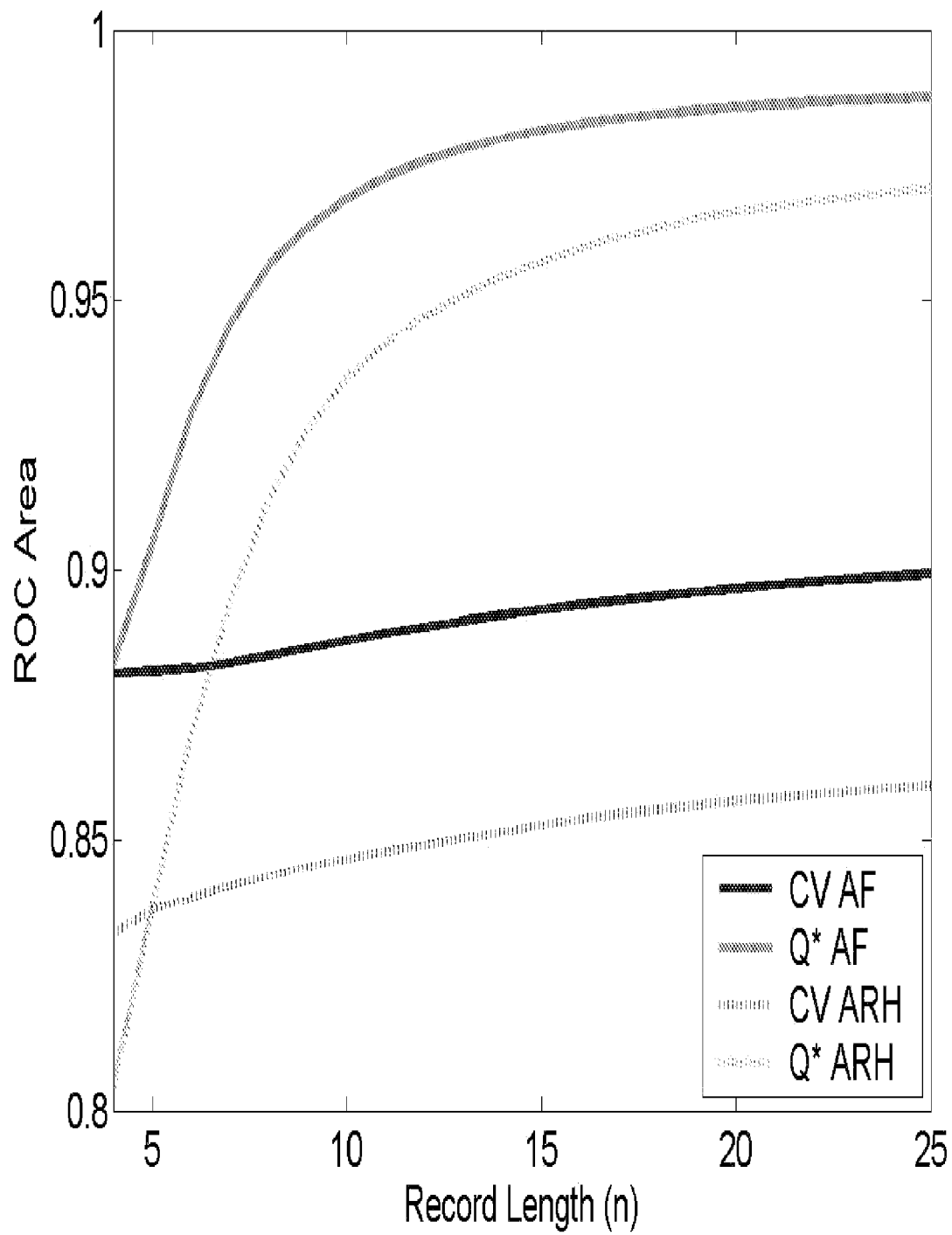
FIG. 5 shows AF detection performance in short RR interval time series.

For patients with severe heart disease, increased risk of ventricular tachycardia (VT), or fibrillation, and especially for patients with implantable cardioverter-defibrillator (ICD) devices, rapidity of diagnosis is paramount. Thus, embodiments of the present invention quantify the diagnostic performance of COSEn over short record lengths in comparison to a common variability measure, the coefficient of variation CV. FIG. 5 is a plot of ROC area as a function of record length for AF detection performance comparing COSEn (Q*) to CV on the AF and ARH databases for all possible overlapping records. In FIG. 5, the ordinate is receiver-operating characteristic (ROC) area. In the inset, CV is coefficient of variation and Q* is COSEn. AF is the MIT-BIH Atrial Fibrillation Database, and ARH is the MIT-BIH Arrhythmia Database. Using CV, the ROC areas for detecting AF are 0.8 to 0.9, and change little for sequences between 4 and 25 beats in length. The ROC areas using COSEn are higher, especially when 10 or more beats are considered.

The improved performance of COSEn was evident even for records with fewer than 10 beats, and remained significantly higher than the performance of CV for lengths as short as 5 beats.

We define the COSEn as the sample entropy of a series after being normalized by the mean. This is equivalent to subtracting the natural logarithm of the mean from the original entropy. To see this, note that if X has mean $\mu$, then $Y=X/\mu$ has mean 1 and density $\mu f(\mu y)$. So the entropy of Y is related to the entropy of X by $$H(Y) = \int_{-\infty}^{\infty} -\log(\mu f(\mu y))\mu f(\mu y) dy = H(X) - \log(\mu)$$

as stated. Similar results can be shown for all Renyi entropy rates and in particular for the differential quadratic entropy rate Q calculated using the SampEn algorithm. This leads the calculation $$Q^* = Q - \log(\mu)$$

where Q* is the coefficient of sample entropy. As shown below, this modification of entropy rate provides a very powerful univariate statistic for classifying AF as part of this invention. In practice, the mean can be estimated with the sample mean or sample median or other robust measures that minimize the effect of noisy, missed, and added beats.

Embodiments of the present invention involve Estimating Entropy Using Matches.

To effectively detect cardiac rhythms, there is a need to be able to process short records of RR intervals that possibly includes missed beats due to noise in the EKG or other limitations of the heart monitoring device. An aspect of various embodiments of the present invention includes novel methods to accurately estimate entropy in this setting using the intuitive notion of matches. A match occurs when all the components of between two distinct templates $X_i(m)$ and $X_j(m)$ are within a specified tolerance r. The total number of matches for template $X_i(m)$ is denoted by $A_i(m)$. For m=0, $A_i(0)$ is equal to the maximum number of possible matches which is n if self-matches are included and otherwise n−1. An estimate of the conditional probability of $X_i$ given (m) is $$\hat{p}_i = \hat{p}_i(m) = \frac{A_i(m+1)}{A_{i-1}(m)}$$

and the corresponding estimate of the density is $$\hat{f}_i = \hat{p}_i/(2r)$$

The estimate of the entropy rate becomes $$\hat{H} = -\frac{1}{n}\sum_{i=1}^{n}\log(\hat{f}_i)$$

$$= -\frac{1}{n}\sum_{i=1}^{n}\log(p_i) + \log(2r)$$

and $$R_q = \frac{1}{1-q}\log\left(\frac{1}{n}\sum_{i=1}^{n}\hat{p}_i^{q-1}\right) + \log(2r)$$

is the estimate of the general conditional Renyi entropy rate. In the sums above, all observations are shown while the conditional probability estimates are not always defined. In this case, they can be defined by some convention or left out of the sum with the option of adjusting the divisor n to reflect these omissions.

The analog of sample entropy, i.e. the quadratic differential entropy rate, is estimated by $$\hat{Q} = -\log\left(\frac{A(m)}{B(m)}\right) + \log(2r)$$

where $$A(m) = \sum_{i=1}^{n} A_i(m+1)$$

and $$B(m) = \sum_{i=1}^{n-1} A_i(m)$$

are the total number of matches of length m+1 and m. Note that most all of the above expressions involve slightly modified manipulation of the fundamental summary statistics $A_i(m)$.

These estimates involve taking logarithms of ratios that become inaccurate or undefined when the numerator and or the denominator are not sufficiently large. This becomes less likely an issue using the total number of matches, and this is a main reason that SampEn has proven to be a more reliable and robust statistic for analyzing heart rate variability. Self-matches are included in the definition of ApEn to overcome problems of infinite or indeterminate ratios, but it still can suffer from significant loss of accuracy when the number of matches is small.

In order to improve the accuracy of ApEn and other conditional entropy rates, we introduce an algorithm that only calculates ratios with specified minimum values of the numerator and denominator, denoted respectively by $n_0$ and $d_0$. The conditional distribution of each observation can be calculated using increasing number of previous observations, but at some template length the number of matches fall below the prescribed minimum. To avoid this possibility, we define a new conditional density estimate $$\hat{f}_i^*(m) = f_i(m^*)$$

where $$m^* = m^*(i) = \max_{0 \leq k \leq m} \{A_i(k+1) \geq n_0, A_{i-1}(k) \geq d_0\}$$

for each m and observation i. This algorithm ensures that each individual contribution to the sums in (30) or (32) has some minimum degree of statistical reliability. This also enables the inclusion of long template matches when they are present and facilitates the goal of not fixing m and estimating the limiting parameters.

Embodiments of the present invention involve estimating the Standard Error of Sample Entropy and COSEn.

The above methods, which apply to calculations of conditional entropy rates, need to be expanded slightly to allow for application to methods using the sample entropy. Recall that for a sequence of data, a set of m consecutive points is called a template and can be considered a vector. An instance where all the corresponding components of two such vectors are within a distance r of each other is called a match. Let $B_i$ and $A_i$ denote the number of matches with templates starting with the $i^{th}$ point of the sequence of lengths m and m+1. respectively. Then the total number of matches of length m and m+1 are $$A = \sum_{i=1}^{N-m} A_i \text{ and } B = \sum_{i=1}^{N-m} B_i.$$

The conditional probability p of a match of length m+1 given a match of length m can then be estimated by p=A/B. As presented in [16], the standard error of p can be estimated by $$\sigma_p^2 = \frac{\sigma_A^2}{B^2} - 2A\frac{\sigma_{AB}^2}{B^3} + A^2\frac{\sigma_B^2}{B^4}$$

where $\sigma_A^2$ is the variance of A, $\sigma_B^2$ is the variance of B, and $\sigma_{AB}^2$ is the covariance between A and B. The sample entropy is equal to $-\log(p)$ and the corresponding estimate of the standard error is $\sigma_p/p$.

Using a methodology similar to that introduced in Lake D E, Renyi entropy measures of heart rate Gaussianity. IEEE Transactions on Biomedical Engineering, Volume 53(1):21-27, 2006, results in the following estimates $$\sigma_A^2 = \frac{N-m}{4} \sum_{k=-K}^{K} \sum_{i=1}^{N-k} (A_i - \overline{A})(A_{i+k} - \overline{A})$$

$$\sigma_{AB}^2 = \frac{N-m}{4} \sum_{k=-K}^{K} \sum_{i=1}^{N-k} (A_i - \overline{A})(B_{i+k} - \overline{B})$$

$$\sigma_B^2 = \frac{N-m}{4} \sum_{k=-K}^{K} \sum_{i=1}^{N-k} (B_i - \overline{B})(B_{i+k} - \overline{B})$$

where $\overline{A}=A/(N-m)$, $\overline{B}=B/(N-m)$, and K is the maximum lag at which the sequences $\{A_i\}$ and $\{B_i\}$ have significant correlation. These estimates differ from those provided in [16] in that they do not fully account for all the dependencies present in the calculations. The advantage of these expressions, especially for processing large amounts of data as is done in this paper, is that they require less computation and preliminary comparison of the methods suggest that they agree favorably with the more accurate method.

The optimal determination of K is application dependent, but the nature of the calculations suggests that a minimum value of m is required. A conservative approach used in this work selects the value that results in the largest variance. The factor of 4 in the above expressions comes from the fact that the expressions for A and B count each match twice.

The coefficient of sample entropy involves a first term with the sample entropy and second term involving the natural logarithm of the sample mean. The standard deviation of COSEn to take into account the additional variation of this second term which can be reasonably assumed to be uncorrelated with the sample entropy term. The standard deviation of the sample mean $\overline{x}$ can be estimated by $s/\sqrt{n}$ where s is the sample standard deviation and n is the length of the segment of RR intervals being analyzed. Then the standard deviation of Q*, denoted by $\sigma^*$, can be estimated by:

$$\sigma^* = \sqrt{\frac{\sigma_p^2}{p} + \frac{s^2}{n\overline{x}^2}} = \sqrt{\frac{\sigma_p^2}{p} + \frac{CV^2}{n}}$$

where CV is the coefficient of variation.

Figure 7:
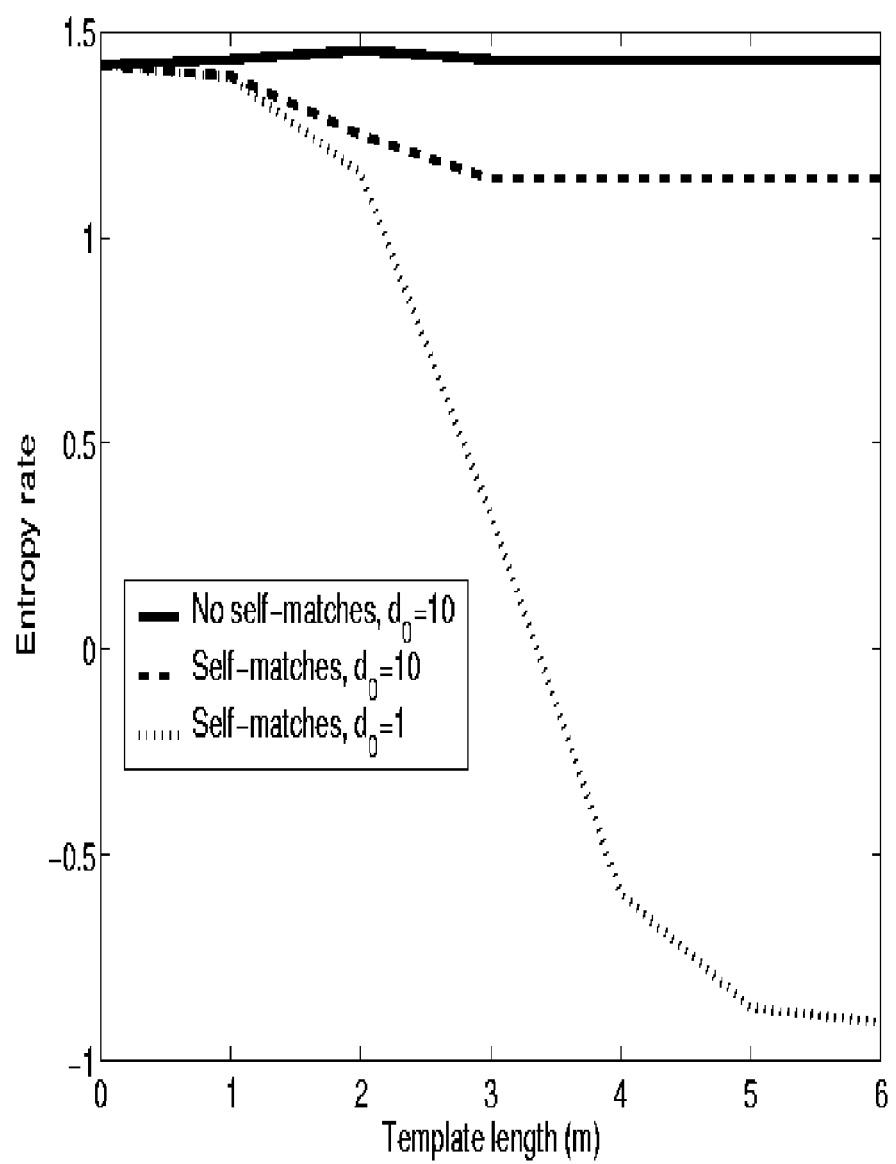
FIG. 7 shows mean of entropy rate estimation algorithms for 100 simulations of Gaussian white noise (n=4096) with theoretical value of 1.4189 for all m.

To demonstrate the robustness of the new algorithm, FIG. 7 shows the mean results of estimating the entropy rate for 100 simulations of Gaussian white noise (n=4096). The tolerance r was set to 0.2 times the sample standard deviation for these and other entropy estimates shown below. The variants of the algorithms shown are no restrictions on the denominator ($d_0$=1) with self-matches, $d_0$=10 with self-matches, and $d_0$=10 without self-matches. In all cases, $n_0$=1 to avoid taking the logarithm of 0. The standard error for all these estimates is less than 0.002. The unrestricted estimate is analogous to the traditional ApEn algorithm which clearly starts to rapidly degenerate after m=2. With $d_0$=10 and the new algorithm, the estimates converge to stable values of on average 1.143 with self-matches and 1.433 without. This latter result agrees favorably with the theoretical value of $(\log(2\pi)+1)/2=1.419$ and is an indication of the improved accuracy of the new invention.

The present invention involves segmentation of heart rate data into homogeneous cardiac rhythms.

Characterizing heart rate data containing 2 or more different rhythms presents a significant challenge. While analyzing short records helps to mitigate this problem, a better solution is to restrict analysis to segments that have been identified as likely containing a homogeneous cardiac rhythm. Homogeneity can be defined, for example, in terms of the mean, standard deviation, or other parameters of the RR interval distribution. Additionally, characteristics of the dynamics of a segment, such as the entropy or correlation function, can be parameters to consider. For a set of parameters, the homogeneity of a segment can be measured based on the "goodness of fit" with some objective function which increases as a segment becomes more nonhomogeneous. A simple example would be the sum of squared deviations of the RR intervals from the mean of a segment. Note that the self-matches, $d_0=1$ curve, corresponding to the traditional approximate entropy algorithm, quickly degenerates after $m=2$. In the same spirit as impurity measures for Classification and Regression Trees (CART) and wavelet packets, this objective function can be termed "entropy." To accomplish this goal, we employ a novel method that automatically optimally divides heart rate data into homogeneous segments. The methodology will be based on an algorithm we call Minimum Piecewise Entropy. Minimum Piecewise Entropy was originally developed to detect transient sonar signals and is described below.

The approach is to hypothesize that the data is made up of some number of homogeneous segments and to optimally estimate the number k and location of change points where the process is altered in some manner such as a shift in the mean. If the data is already homogeneous, the algorithm should ideally estimate k to be 0 and no segmentation would occur. The entropy of each stationary segment of data is calculated and the criteria for optimality will be the piecewise entropy of the data which is calculated as the sum of the individual components. As mentioned above, entropy could be any of a variety of measures including the sum of the squares of the residuals or the log-likelihood function after a particular model has been fit to the data.

Once a criterion has been determined, the problem becomes how to select among the all the possible ways a set of N points could be partitioned into k segments. Fortunately, there exists an efficient dynamic programming algorithm to do this optimization. To see this let $E(i,j)$ denote the minimum entropy for $x(i)$, $x(i+1)$, ..., $x(j)$. Also define $e(j)=E(1,j)=$minimum piecewise entropy for $x(1)$, $x(2)$, ..., $x(j)$. The minimum piecewise entropy can be found efficiently using dynamic programming because the entropy is assumed additive, that is, $E(i,j)=E(i,k)+E(k+1,j)$. The recursive algorithm to find the minimum piecewise entropy e is $e(0)=0$ and $$e(j)=\min_{1\le i\le k}\{e(i-1)+E(i,j)\}$$

for $j=1, 2, \ldots, N$.

All else being equal, fewer change points are preferable in estimating the piecewise entropy. The algorithm for minimum piecewise entropy can be modified slightly to estimate the entropy using a certain number of change points. Define $e(j,k)=$minimum piecewise entropy for $x(1)$, $x(2)$, ..., $x(j)$ using k change points and the recursive algorithm generalizes to $e(0,k)=0$ and $$e(j,k)=\min_{1\le i\le k}\{e(i-1,k-1)+E(i,j)\}$$

for $k=0, 1, \ldots, K$ and $j=1, 2, \ldots, N$ where K is some specified upper bound.

EXAMPLES

Various embodiments of the present invention, and the improved results obtained therefrom, are illustrated by way of the following, non-limiting examples.

Results from the method of the present invention method have been compared to the KS distance method of Tateno and Glass in the canonical and publicly available MIT-BIH AF Database. Representative predictive models perform well in detecting AF, as assayed by receiver-operating characteristics (ROC) areas as shown later. Note that the method of various embodiments of the present invention only requires a few coefficients for implementation regardless of number of AF patients used to train model. This is more efficient than repeated comparisons to multiple histograms, as is called for in the KS distance method of Tateno and Glass.

Example 1 Relates to AF Detection in the MIT-BIH Databases

In these examples univariable and multivariable methods were used to classify cardiac rhythms, employing logistic regression and its variations. Segments of 50-point non-overlapping records are separated into binary outcomes with 1 denoting normal sinus rhythm or 0 denoting a cardiac arrhythmia such as atrial fibrillation. A variety of the moment and entropy rate parameters described above are estimated for each record and cardiac rhythm classifiers are developed using an optimal parsimonious subset of variables.

For purposes of this example, an optimal subset of variables for the MIT-BIH Atrial Fibrillation Database is the quadratic differential entropy rate (Q), the mean ($\mu$), and the standard deviation ($\sigma$) of the RR intervals. The entropy rate is calculated using the SampEn algorithm with parameters $m=1$ and $r=50$ milliseconds. This result aided in the development of the coefficient of sample entropy (Q*) which is described in more detail below. We also compare these results with the coefficient of variation $CV=\sigma/\mu$ Subsets of parameters are evaluated using the significances of individual coefficients and of the overall model using the Wald statistic adjusted for repeated measures. The overall significance of the model can be converted to a Wald Z-statistic which can be used to make a fair comparison among models with varying number of parameters. The models are also verified on the independent MIT-BIH Arrhythmia Database. The database is divided into 2075 non-overlapping 50 point records with 184 (8.9%) AF records.

The results of this analysis are summarized below in Table 2. The parameter TG represents results using the KS distance method of Tateno and Glass.

TABLE 2

Model Performances on MIT-BIH AF data base

| Parameters | AF ROC | Wald | Wald Z | ARH ROC |
|---|---|---|---|---|
| log(CV) | 0.913 | 25.0 | 17.0 | 0.862 |
| Q | 0.988 | 85.2 | 59.6 | 0.976 |
| TG | 0.992 | 38.1 | 26.3 | 0.976 |
| Q, log($\mu$), log($\sigma$) | 0.995 | 82.4 | 32.4 | 0.985 |
| Q* | 0.995 | 59.1 | 41.1 | 0.985 |

Example 2—AF Detection in 422 Consecutive Holter Monitor Recordings

Figure 2:
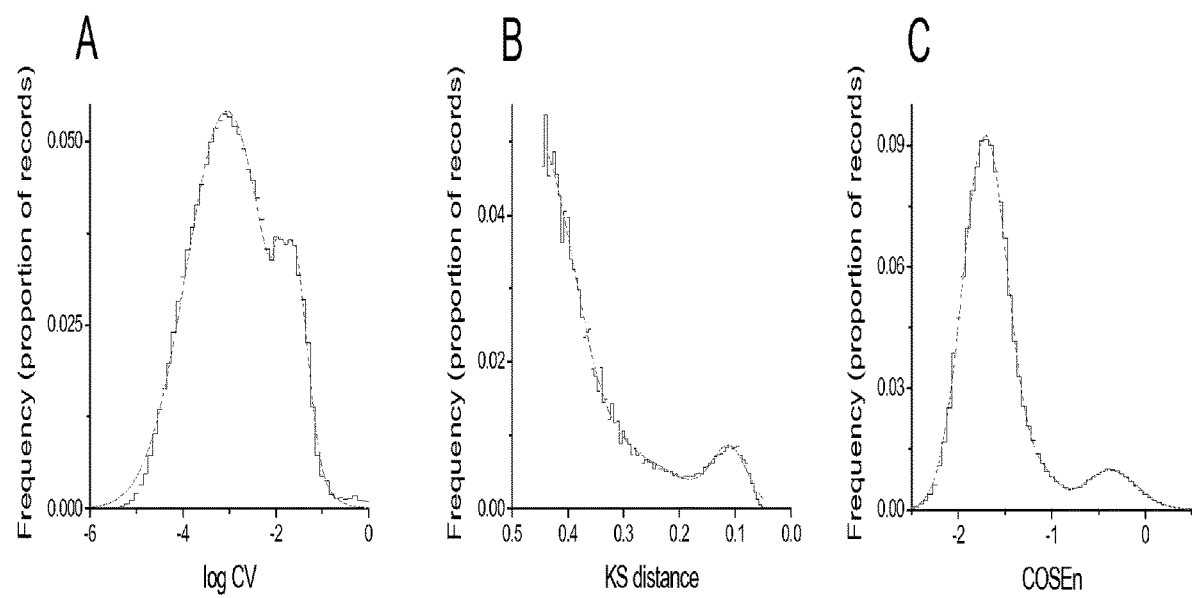
FIG. 2 shows frequency histograms of time series measures in 422 24-hour Holter monitor records from the University of Virginia Heart Station.

In 920, 242 50-beat records we calculated CV, KS distance (that is, we implemented the method of Tateno and Glass), and COSEn. FIG. 2 shows frequency histograms of the results, i.e., of time series measures in 422 24-hour Holter monitor records from the University of Virginia Heart Station.

The multimodal nature suggests that different components contribute to the overall distribution. We dissected the components using sums of 3 Gaussians functions, shown as smooth lines representing an expression of the form:

$$f(x) = \frac{A_1}{\sigma_1\sqrt{2\pi}}e^{-(x-\mu_1)^2/2\sigma_1^2} + \frac{A_2}{\sigma_2\sqrt{2\pi}}e^{-(x-\mu_2)^2/2\sigma_2^2} + \frac{A_2}{\sigma_2\sqrt{2\pi}}e^{-(x-\mu_2)^2/2\sigma_2^2},$$

where A is the proportion of the total area attributed to each component, and μ and σ are the mean and standard deviation of each component.

The largest component is attributed to normal sinus rhythm (NSR), and the next largest is attributed to atrial fibrillation (AF). The smallest, which always is intermediate in location, is attributed to premature ventricular contractions (PVCs) and premature atrial contractions (PACs). These assignments are borne out qualitatively by inspection of individual records. A limitation, though, to this analysis is that we have not verified the rhythm labels of every beat. We know from inspection of some of the records, that the labeling is not altogether accurate. In each case, the numerical analyses were correct in classifying the rhythm label.

There was reasonable agreement about the relative proportions of rhythm labels using the CV, KS distances, and COSEn. The proportions of NSR were 0.87, 0.81 and 0.85, respectively, and the proportions of AF were 0.12, 0.06 and 0.11, respectively. The most important differences lie in the detected AF burdens—6% in the Tateno-Glass KS distance method and 11% using the new COSEn measure. The burden of other rhythms is even more different—13% compared with 4%, respectively.

Another important finding is a sensible cut-off for detecting AF using COSEn. Both by visual inspection of the histogram and by analysis of the Gaussian fit, we select COSEn=−1 as a threshold value, and we classify records with lower values as NSR and higher values as AF. Analysis of the areas of the components of the sum of 3 Gaussians fit suggest that 11% of data are misclassified using COSEn compared with 28% using CV and 8% using KS distances.

Example 3 Relates to AF Classification in 24-Hour Holter Recordings Using COSEn

Figure 3:
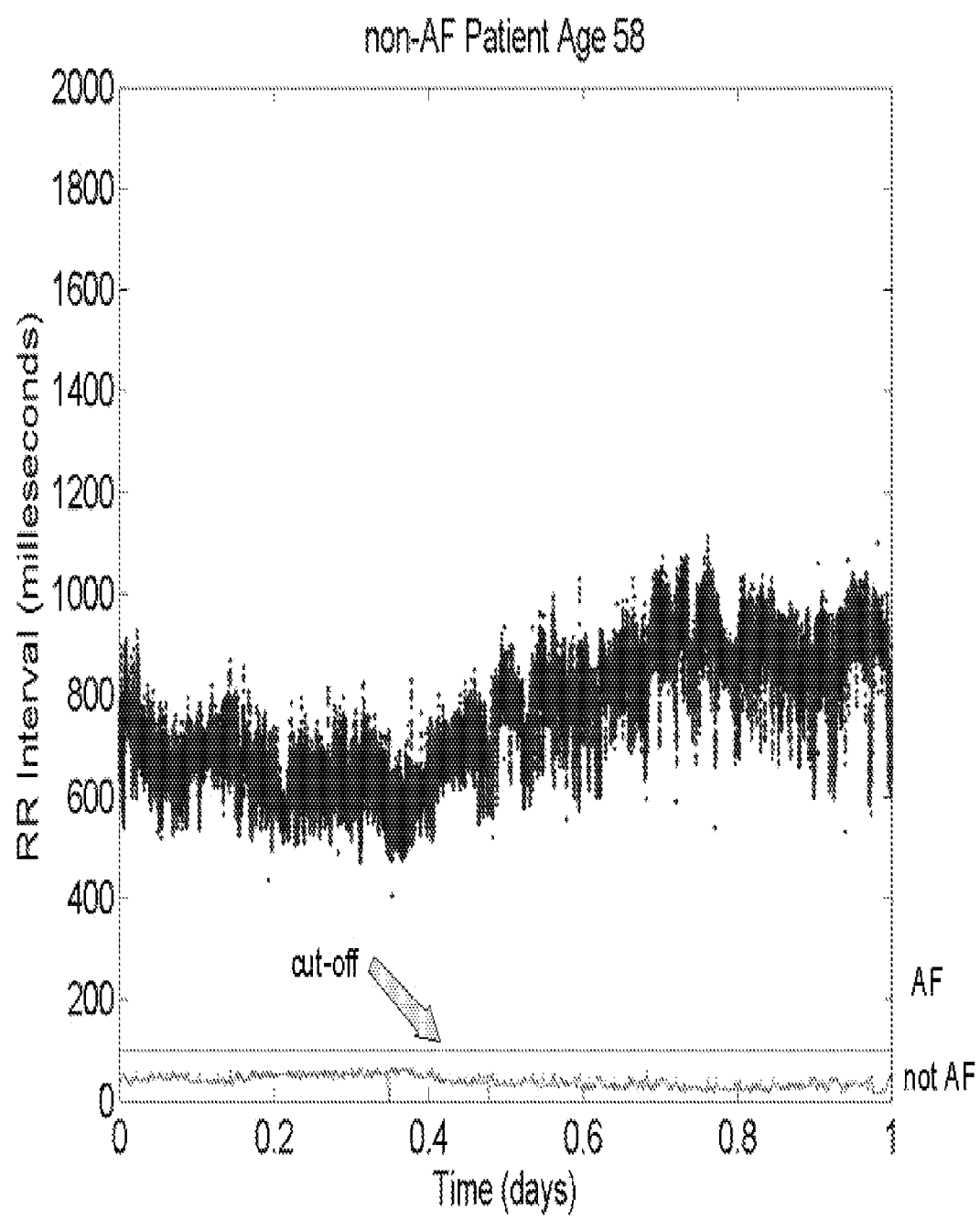
FIG. 3 shows a 24-hour Holter recording from a patient in NSR throughout the recording, demonstrated by blue RR interval data points. The purple line at the bottom is COSEn, and the arrow marks the threshold above which AF is diagnosed.
Figure 4:
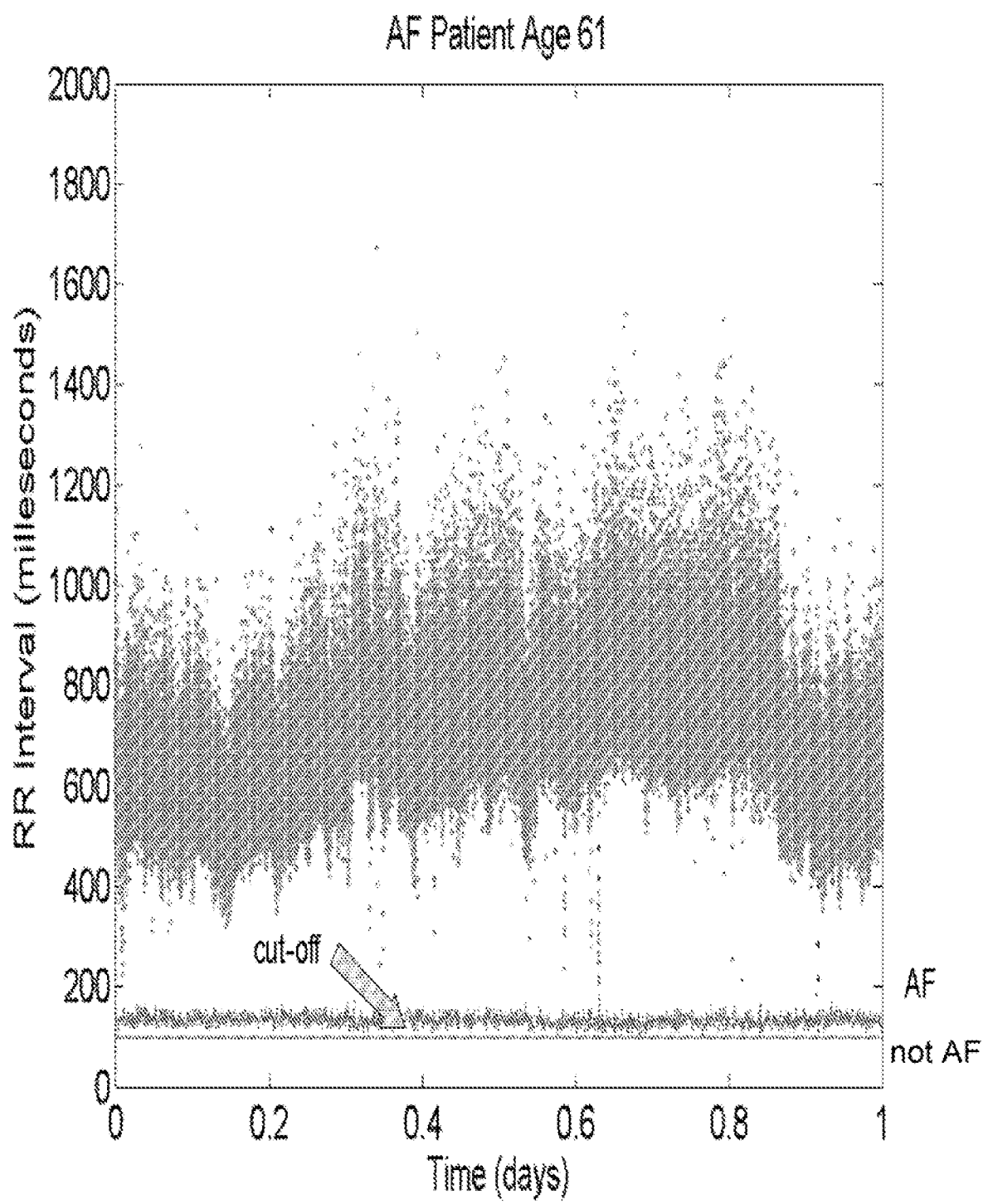
FIG. 4 shows a 24-hour Holter recording from a patient in AF throughout the recording, demonstrated by green RR interval data points. The purple line at the bottom is COSEn, and the arrow marks the threshold above which AF is diagnosed.

FIGS. 1, 3, and 4 show three of the 24-hour Holter monitor recordings, and RR intervals are classified as NSR (blue) or AF (green) using only COSEn, which is shown as a purple line at the bottom. The cut-off of COSEn=−1 was chosen by eye from inspection of the frequency histogram of COSEn values in 420 consecutive Holter recordings. FIGS. 3 and 4 show uninterrupted NSR and AF, respectively. FIG. 1 shows a record with paroxysms of AF. There is good agreement between the COSEn value and the appearance of the time series. Note that the y-axis is RR interval, and AF is characterized by faster rates (shorter intervals) as well as increased variability.

Example 4—Finding Optimal Segmentation for MIT-BIH Arrhythmia Data Base

The minimum piecewise entropy algorithm was applied to the MIT-BIH Arrhythmia Database prior to applying our logistic regression model to predict the presence of atrial fibrillation train on the MIT-BIH atrial fibrillation database. The algorithm was applied to pick the optimal change points for segments with homogeneous mean and variance. The optimal number of change points was selected using a penalty based on the number of segments and the length of the data record as previously described (See Lake D E. Efficient adaptive signal and signal dimension estimation using piecewise projection libraries Wavelet Applications V, H. H. Szu, Editor, Proc. SPIE Vol. 3391, p. 388-395, 1998, and Lake D E. Adaptive signal estimation using projection libraries (Invited Paper) Wavelet Applications IV, H. H. Szu, Editor, Proc. SPIE-3078, p.p. 602-609, 1997.).

Figure 6:
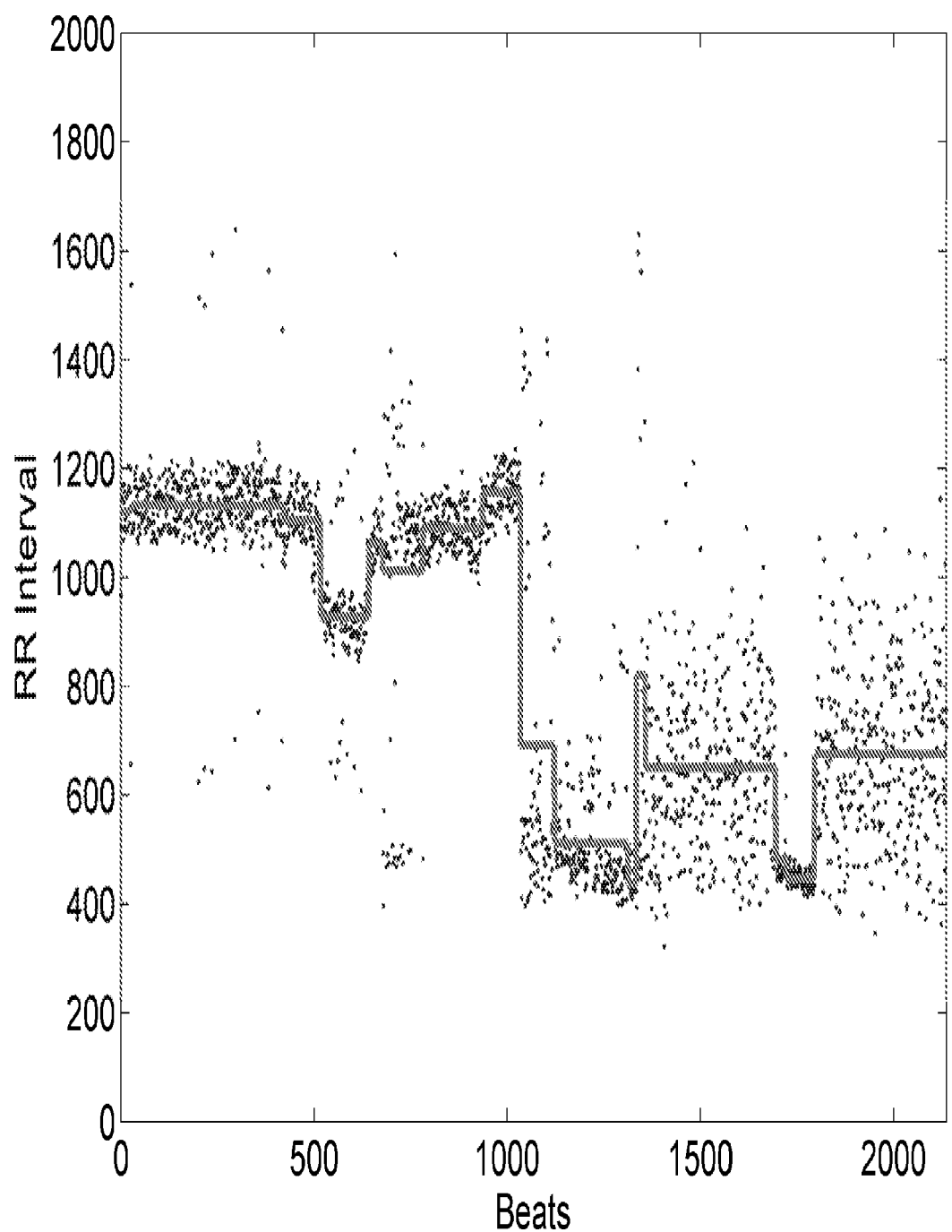
FIG. 6 shows optimal segmentation of RR interval time series using an entropy-based method of the result for subject 202 in the MIT-BIH Arrhythmia Database (See also FIG. 1 in K. Tateno and L. Glass, "Automatic detection of atrial fibrillation using the coefficient of variation and density histograms of RR and ΔRR intervals," Med Biol Eng Comput vol. 39, 664-671, 2001.)

An example is shown in FIG. 6. The optimal number of segments was found to be 18 with lengths ranging from 22 to 341 beats.

This procedure was repeated for all 48 subjects in the database resulting in 525 homogeneous segments. The moments and entropy for each segment were calculated and evaluated for the presence of AF.

Table 3, summarizes the results with a threshold of 0.8 and compares the results to the method of Tateno and Glass (as summarized in Table 3 of K. Tateno and L. Glass, "Automatic detection of atrial fibrillation using the coefficient of variation and density histograms of RR and ΔRR intervals," Med Biol Eng Comput vol. 39, 664-671, 2001.)

TABLE 3

| Method | TP | TN | FN | FP | Sens. | Spec. |
|---|---|---|---|---|---|---|
| Tateno-Glass | 10218 | 89973 | 1371 | 6176 | 88.2% | 93.6% |
| COSEn | 11534 | 94383 | 667 | 2910 | 94.5% | 97.0% |

Thus the new method has superior performance characteristics in this canonical database.

Example 5—Optimal Segmentation in Near-Real Time

This example demonstrates an alternative embodiment of the optimal segmentation process according to the present invention. An advantage of this embodiment is exact identification of start and stop times of AF. To preserve near-real time performance, it is implemented only when the rhythm is perceived to change into or out of AF.

An evaluation of the MIT ARH and AF databases using American National Standards ANSI/AAMI EC38:1998 was conducted to evaluate COSEn performance on AF detection in the MIT ARH and AF databases. The 50 previous and the 50 subsequent beats were used to identify homogenous segments for classification using COSEn. This requires a delay of 50 beats, and the algorithm is considered near-real time.

The following order of operations was employed: (1) COSEn was calculated on non-overlapping 16 beat segments; (2) beats were labeled in each segment as AF or non-AF based on a threshold value determined from the UVa Holter database; (3) when the label changed, the near-real time segmentation analysis was implemented to determine whether there was a statistically significant change in the rhythm and, if so, the exact beat at which the label should change; (4) in the ARH database, any segments with more than 25% of beats labeled as ectopic were classified and labeled as non-AF. Results are displayed in Tables 4 and 5. Note that the output is in standard sumstats format.

TABLE 4

MIT ARH database results

| Record | TPs | FN | TPp | FP | ESe | E + P | DSe | D + P | Ref duration | Test duration |
|---|---|---|---|---|---|---|---|---|---|---|
| 100 | 0 | 0 | 0 | 0 | — | — | — | — | 0.000 | 0.000 |
| 101 | 0 | 0 | 0 | 0 | — | — | — | — | 0.000 | 0.000 |
| 102 | 0 | 0 | 0 | 0 | — | — | — | — | 0.000 | 0.000 |
| 103 | 0 | 0 | 0 | 0 | — | — | — | — | 0.000 | 0.000 |
| 104 | 0 | 0 | 0 | 0 | — | — | — | — | 0.000 | 0.000 |
| 105 | 0 | 0 | 0 | 0 | — | — | — | — | 0.000 | 0.000 |
| 106 | 0 | 0 | 0 | 0 | — | — | — | — | 0.000 | 0.000 |
| 107 | 0 | 0 | 0 | 0 | — | — | — | — | 0.000 | 0.000 |
| 108 | 0 | 0 | 0 | 0 | — | — | — | — | 0.000 | 0.000 |
| 109 | 0 | 0 | 0 | 0 | — | — | — | — | 0.000 | 0.000 |
| 111 | 0 | 0 | 0 | 0 | — | — | — | — | 0.000 | 0.000 |
| 112 | 0 | 0 | 0 | 0 | — | — | — | — | 0.000 | 0.000 |
| 113 | 0 | 0 | 0 | 0 | — | — | — | — | 0.000 | 0.000 |
| 114 | 0 | 0 | 0 | 0 | — | — | — | — | 0.000 | 0.000 |
| 115 | 0 | 0 | 0 | 0 | — | — | — | — | 0.000 | 0.000 |
| 116 | 0 | 0 | 0 | 0 | — | — | — | — | 0.000 | 0.000 |
| 117 | 0 | 0 | 0 | 0 | — | — | — | — | 0.000 | 0.000 |
| 118 | 0 | 0 | 0 | 0 | — | — | — | — | 0.000 | 0.000 |
| 119 | 0 | 0 | 0 | 0 | — | — | — | — | 0.000 | 0.000 |
| 121 | 0 | 0 | 0 | 0 | — | — | — | — | 0.000 | 0.000 |
| 122 | 0 | 0 | 0 | 0 | — | — | — | — | 0.000 | 0.000 |
| 123 | 0 | 0 | 0 | 0 | — | — | — | — | 0.000 | 0.000 |
| 124 | 0 | 0 | 0 | 0 | — | — | — | — | 0.000 | 0.000 |
| 200 | 0 | 0 | 0 | 0 | — | 0 | — | 0 | 0.000 | 1:31.952 |
| 201 | 3 | 0 | 2 | 0 | 100 | 100 | 100 | 73 | 10:05.800 | 13:46.688 |
| 202 | 3 | 0 | 3 | 0 | 100 | 100 | 81 | 88 | 9:31.080 | 8:47.475 |
| 203 | 15 | 0 | 1 | 0 | 100 | 100 | 100 | 92 | 22:58.497 | 24:51.286 |
| 205 | 0 | 0 | 0 | 0 | — | — | — | — | 0.000 | 0.000 |
| 207 | 0 | 0 | 0 | 0 | — | — | — | — | 0.000 | 0.000 |
| 208 | 0 | 0 | 0 | 0 | — | — | — | — | 0.000 | 0.000 |
| 209 | 0 | 0 | 0 | 0 | — | — | — | — | 0.000 | 0.000 |
| 210 | 6 | 0 | 1 | 0 | 100 | 100 | 100 | 97 | 29:12.513 | 30:05.555 |
| 212 | 0 | 0 | 0 | 0 | — | — | — | — | 0.000 | 0.000 |
| 213 | 0 | 0 | 0 | 0 | — | — | — | — | 0.000 | 0.000 |
| 214 | 0 | 0 | 0 | 0 | — | — | — | — | 0.000 | 0.000 |
| 215 | 0 | 0 | 0 | 0 | — | — | — | — | 0.000 | 0.000 |
| 217 | 1 | 0 | 1 | 0 | 100 | 100 | 100 | 14 | 0:49.688 | 5:56.738 |
| 219 | 7 | 0 | 4 | 0 | 100 | 100 | 100 | 96 | 23:21.730 | 24:15.705 |
| 220 | 0 | 0 | 0 | 0 | — | — | — | — | 0.000 | 0.000 |
| 221 | 8 | 0 | 1 | 0 | 100 | 100 | 100 | 93 | 27:57.755 | 30:05.555 |
| 222 | 2 | 0 | 2 | 0 | 100 | 100 | 100 | 27 | 5:13.694 | 19:13.733 |
| 223 | 0 | 0 | 0 | 0 | — | — | — | — | 0.000 | 0.000 |
| 228 | 0 | 0 | 0 | 3 | — | 0 | — | 0 | 0.000 | 8:49.361 |
| 230 | 0 | 0 | 0 | 0 | — | — | — | — | 0.000 | 0.000 |
| 231 | 0 | 0 | 0 | 0 | — | — | — | — | 0.000 | 0.000 |
| 232 | 0 | 0 | 0 | 0 | — | — | — | — | 0.000 | 0.000 |
| 233 | 0 | 0 | 0 | 0 | — | — | — | — | 0.000 | 0.000 |
| 234 | 0 | 0 | 0 | 0 | — | — | — | — | 0.000 | 0.000 |
| Sum | 45 | 0 | 15 | 4 | | | | | 2:09:10.757 | 2:47:24.048 |
| Gross | | | | | 100 | 79 | 98 | 76 | | |
| Average | | | | | 100 | 80 | 98 | 58 | | |

Summary of results from 48 records

TABLE 5

MIT AF database results (AF detection)

| Record | TPs | FN | TPp | FP | ESe | E + P | DSe | D + P | Ref duration | Test duration |
|---|---|---|---|---|---|---|---|---|---|---|
| 00735 | 1 | 0 | 1 | 0 | 100 | 100 | 85 | 95 | 4:24.068 | 3:57.740 |
| 03665 | 6 | 0 | 5 | 2 | 100 | 71 | 100 | 98 | 1:39:12.612 | 1:41:13.712 |
| 04015 | 2 | 0 | 1 | 12 | 100 | 8 | 100 | 10 | 3:22.116 | 33:43.156 |
| 04043 | 67 | 4 | 66 | 5 | 94 | 93 | 88 | 92 | 2:08:19.984 | 2:02:40.980 |
| 04048 | 3 | 0 | 3 | 2 | 100 | 60 | 99 | 13 | 4:43.104 | 35:26.516 |
| 04126 | 5 | 0 | 5 | 3 | 100 | 63 | 99 | 87 | 22:18.568 | 25:37.816 |
| 04746 | 2 | 0 | 2 | 0 | 100 | 100 | 100 | 100 | 5:25:16.396 | 5:24:43.176 |
| 04908 | 6 | 1 | 5 | 4 | 86 | 56 | 93 | 91 | 51:04.024 | 52:36.796 |
| 04936 | 26 | 3 | 94 | 0 | 90 | 100 | 70 | 99 | 7:21:33.528 | 5:13:13.296 |
| 05091 | 1 | 0 | 1 | 0 | 100 | 100 | 100 | 78 | 0:42.552 | 0:54.728 |
| 05121 | 16 | 1 | 38 | 1 | 94 | 97 | 91 | 98 | 6:25:57.448 | 5:57:21.352 |

TABLE 5-continued

MIT AF database results (AF detection)

| Record | TPs | FN | TPp | FP | ESe | E + P | DSe | D + P | Ref duration | Test duration |
|---|---|---|---|---|---|---|---|---|---|---|
| 05261 | 2 | 0 | 2 | 7 | 100 | 22 | 100 | 54 | 6:21.796 | 11:50.140 |
| 06426 | 22 | 1 | 19 | 1 | 96 | 95 | 100 | 98 | 9:44:30.812 | 9:51:35.768 |
| 06453 | 2 | 1 | 2 | 1 | 67 | 67 | 50 | 69 | 5:19.072 | 3:51.488 |
| 06995 | 3 | 1 | 7 | 9 | 75 | 44 | 98 | 97 | 4:48:44.452 | 4:51:32.332 |
| 07162 | 1 | 0 | 1 | 0 | 100 | 100 | 100 | 100 | 10:13:42.344 | 10:13:43.040 |
| 07859 | 1 | 0 | 55 | 0 | 100 | 100 | 92 | 100 | 10:13:42.868 | 9:24:53.036 |
| 07879 | 1 | 0 | 6 | 0 | 100 | 100 | 99 | 100 | 6:09:59.948 | 6:08:02.492 |
| 07910 | 3 | 0 | 3 | 0 | 100 | 100 | 98 | 100 | 1:37:33.584 | 1:36:15.664 |
| 08215 | 2 | 0 | 2 | 0 | 100 | 100 | 100 | 100 | 8:14:33.968 | 8:14:08.084 |
| 08219 | 38 | 0 | 25 | 8 | 100 | 76 | 95 | 81 | 2:12:05.500 | 2:35:34.072 |
| 08378 | 3 | 1 | 3 | 8 | 75 | 27 | 93 | 21 | 25:39.508 | 1:53:33.364 |
| 08405 | 1 | 0 | 1 | 1 | 100 | 50 | 100 | 100 | 7:22:51.916 | 7:24:05.300 |
| 08434 | 3 | 0 | 2 | 0 | 100 | 100 | 99 | 92 | 23:43.736 | 25:35.944 |
| 08455 | 2 | 0 | 2 | 0 | 100 | 100 | 100 | 100 | 7:04:31.024 | 7:04:38.284 |
| Sum | 219 | 13 | 351 | 64 | | | | | 93:10:14.928 | 92:50:48.276 |
| Gross | | | | | 94 | 85 | 95 | 96 | | |
| Average | | | | | 95 | 77 | 94 | 83 | | |

Summary of results from 25 records

Excellent performance in the MIT ARH and AF databases does not necessarily translate into robust real-world results, because of various problems with the MIT databases.

The RR interval time series in the ARH database of the 2 patients with AF with the results of our analysis compared with the EKG interpretation. EKG waveforms from some of the disputed areas are shown in FIGS.

Figure 8:
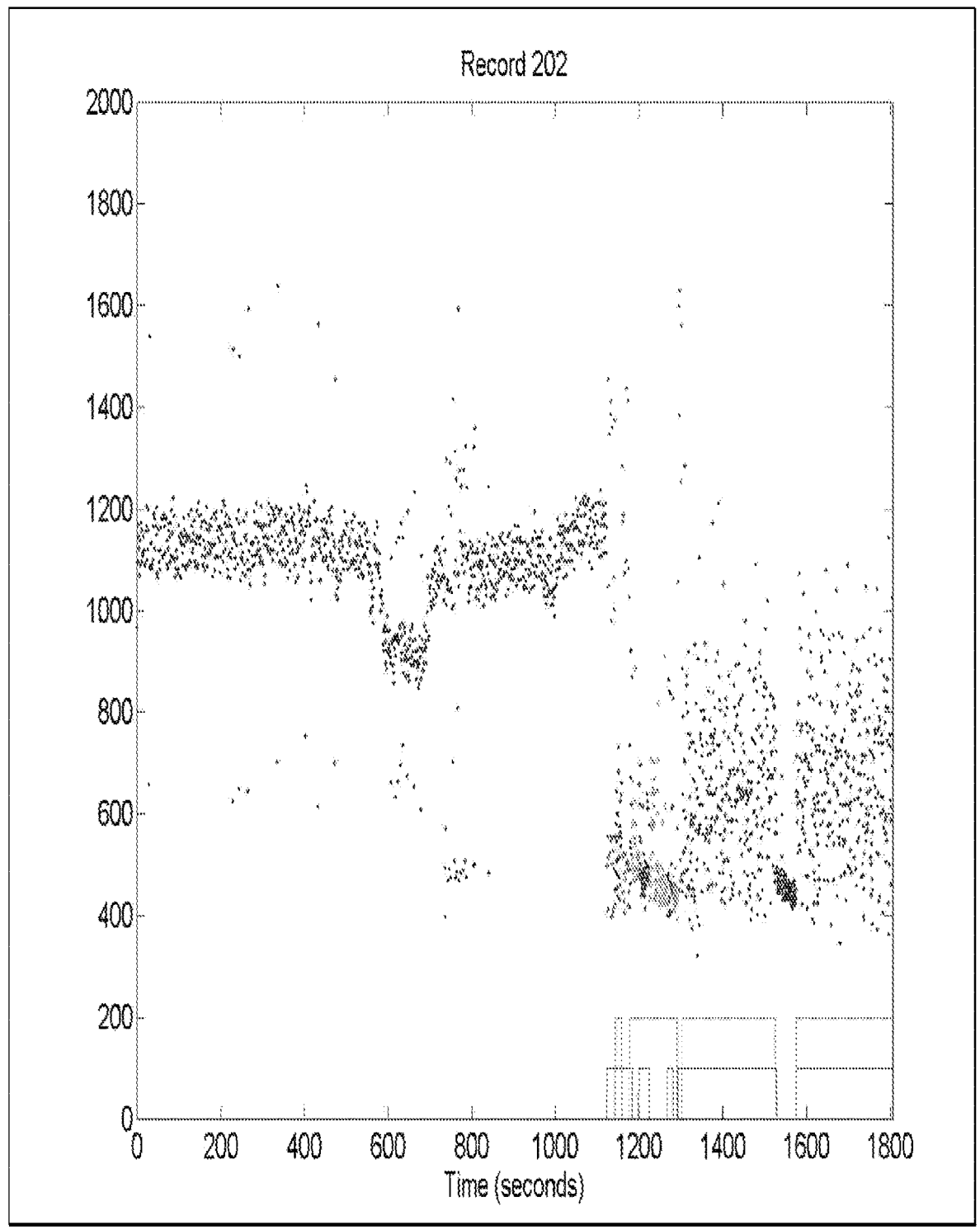
FIG. 8 shows the complete 30 minute RR interval time series of Record 202 in Table 4.

FIG. 8 shows the complete 30 minute RR interval time series from Record 202, a complex record with obvious rhythm changes.

Figure 9:
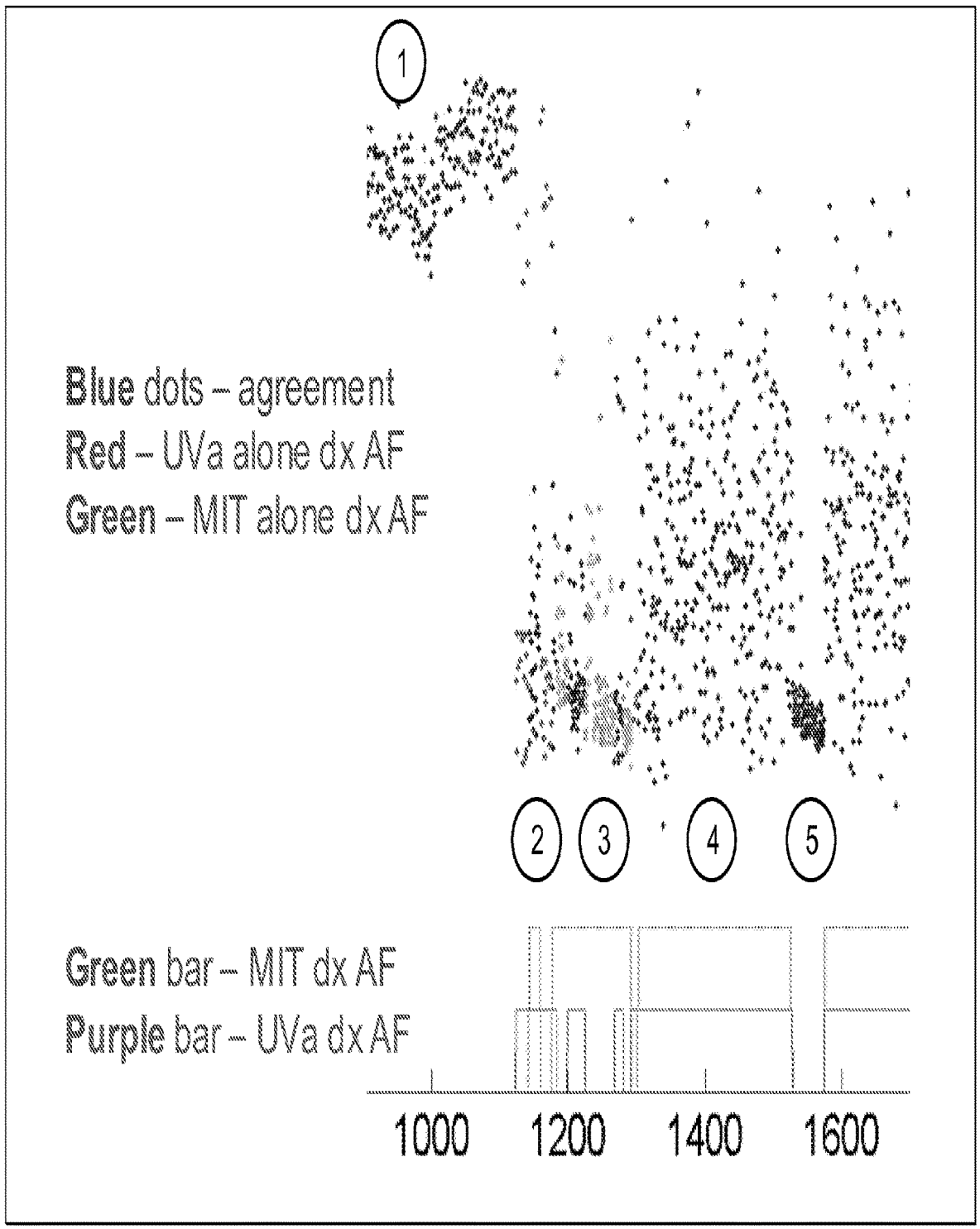
FIG. 9 shows an explanation of Figure labels.

FIG. 9 shows our labeling strategy—blue dots are RR intervals in which we agree with the electrocardiographer who labeled the database, red dots are intervals we labeled as AF but s/he did not, and green dots we did not label as AF but s/he did. The open bars below show duration of AF episodes as labeled by the electrocardiographer (in green), and as detected by our numerical algorithm (in purple).

Several areas are identified by circled numbers, and the corresponding EKG strips are shown.

Figure 10:
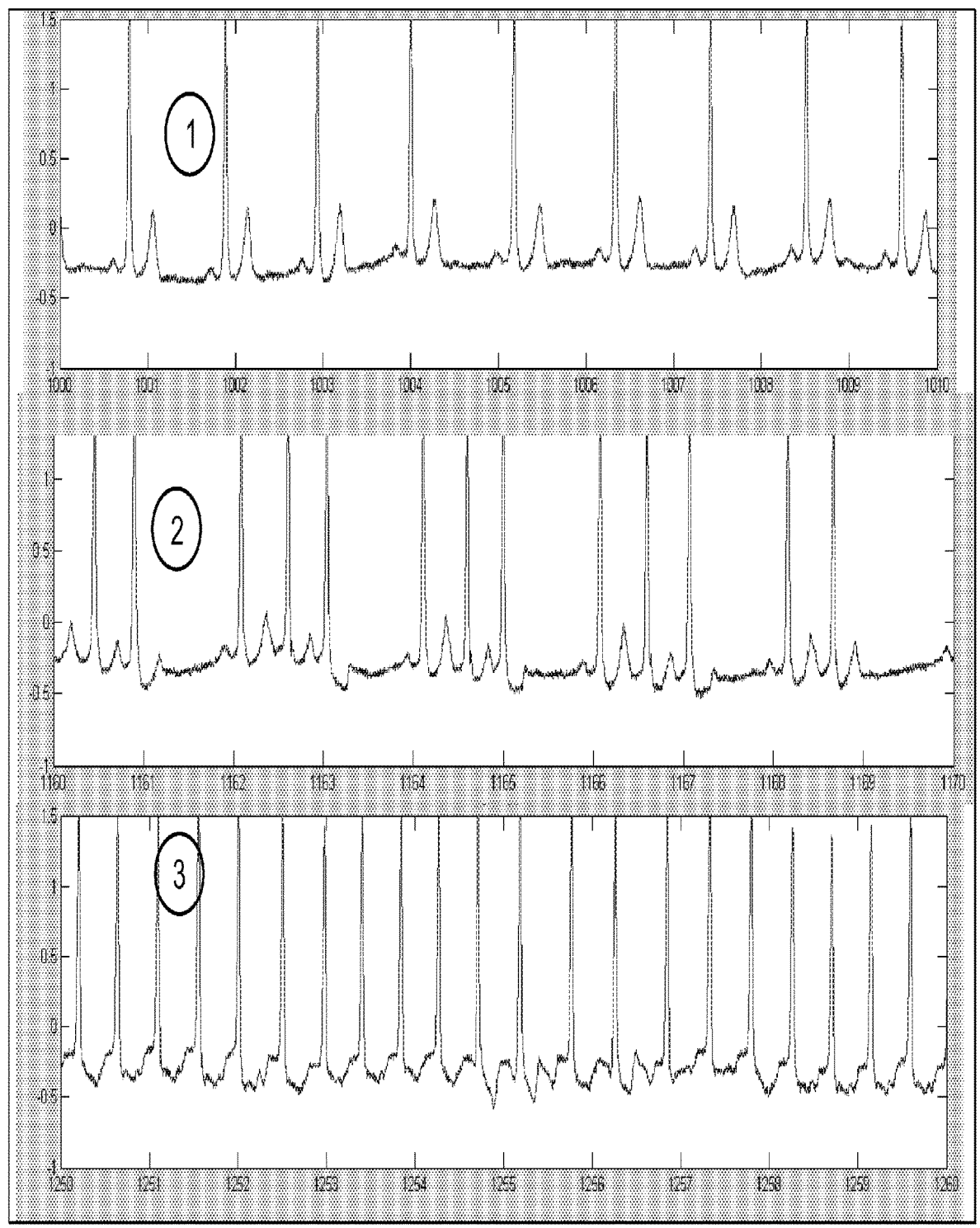
FIG. 10 shows EKG strips from labeled areas of FIG. 8.

Strip 1, in FIG. 10, shows sinus rhythm that we agree on.

Strip 2, in FIG. 10, was detected by us as AF but is obviously not AF—it is sinus rhythm with very, very frequent atrial ectopy. This rhythm is sometimes a harbinger of AF, but is not AF. It is not surprising that we detect it as AF because of its irregularity.

Strip 3, in FIG. 10, was not detected by us as AF but was labeled as AF by the electrocardiographer. Inspection of the entire record shows that the rhythm is AF with varying degrees of organization, or atrial flutter-like qualities. For this epoch, the atrial activity was rather organized resulting in a more regular ventricular rhythm, hence our misdiagnosis. Clinically, the patient would be treated for AF.

Figure 11:
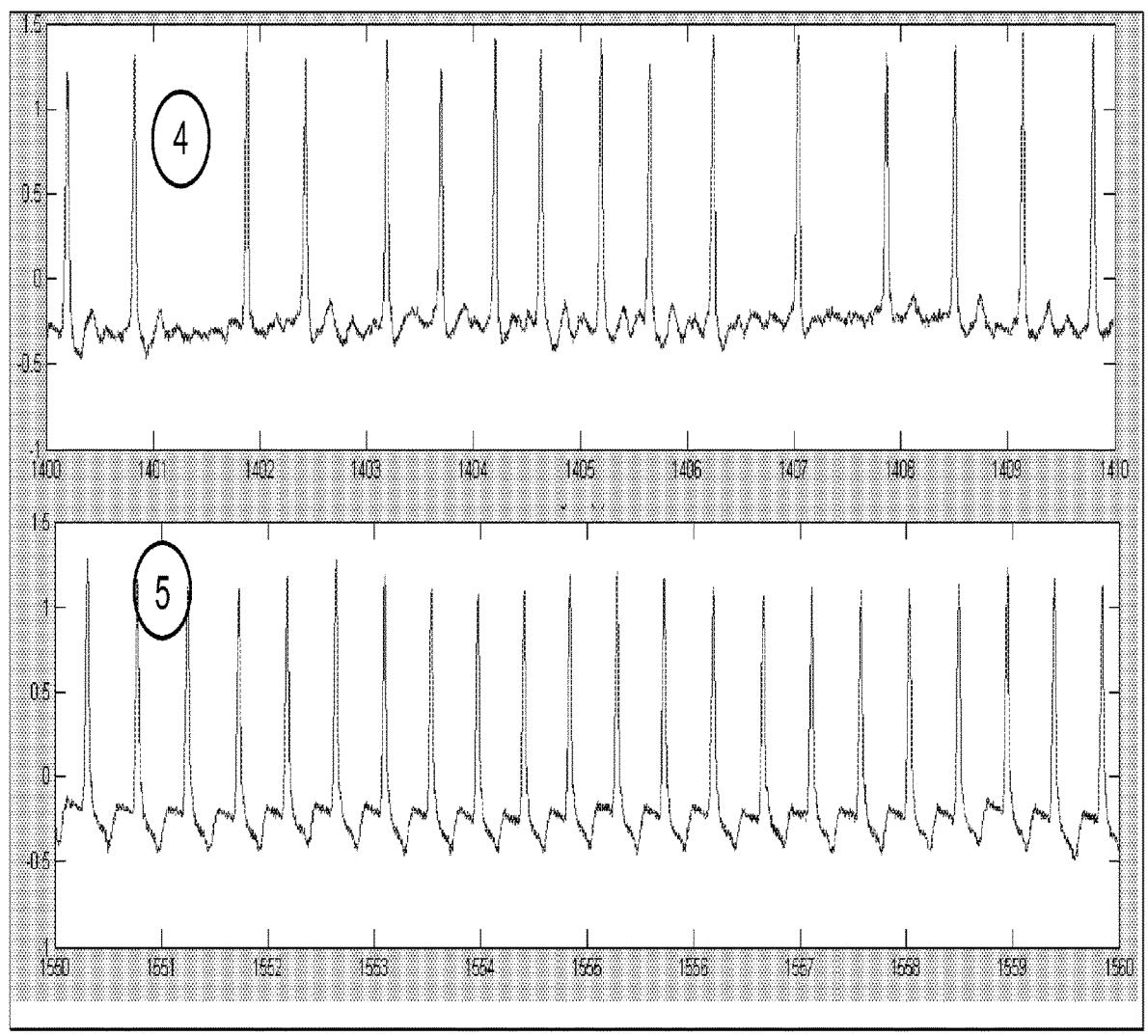
FIG. 11 shows EKG strips from labeled areas of FIG. 8.

Strip 4, in FIG. 11, is clearly AF, and we agree.

Strip 5, in FIG. 11, is essentially identical to strip 3. We called neither AF. The electrocardiographer called the first one AF and the second one atrial flutter. This is inconsistent, and emphasizes the problem with using these databases as the gold standard for arrhythmia diagnostics.

Figure 12:
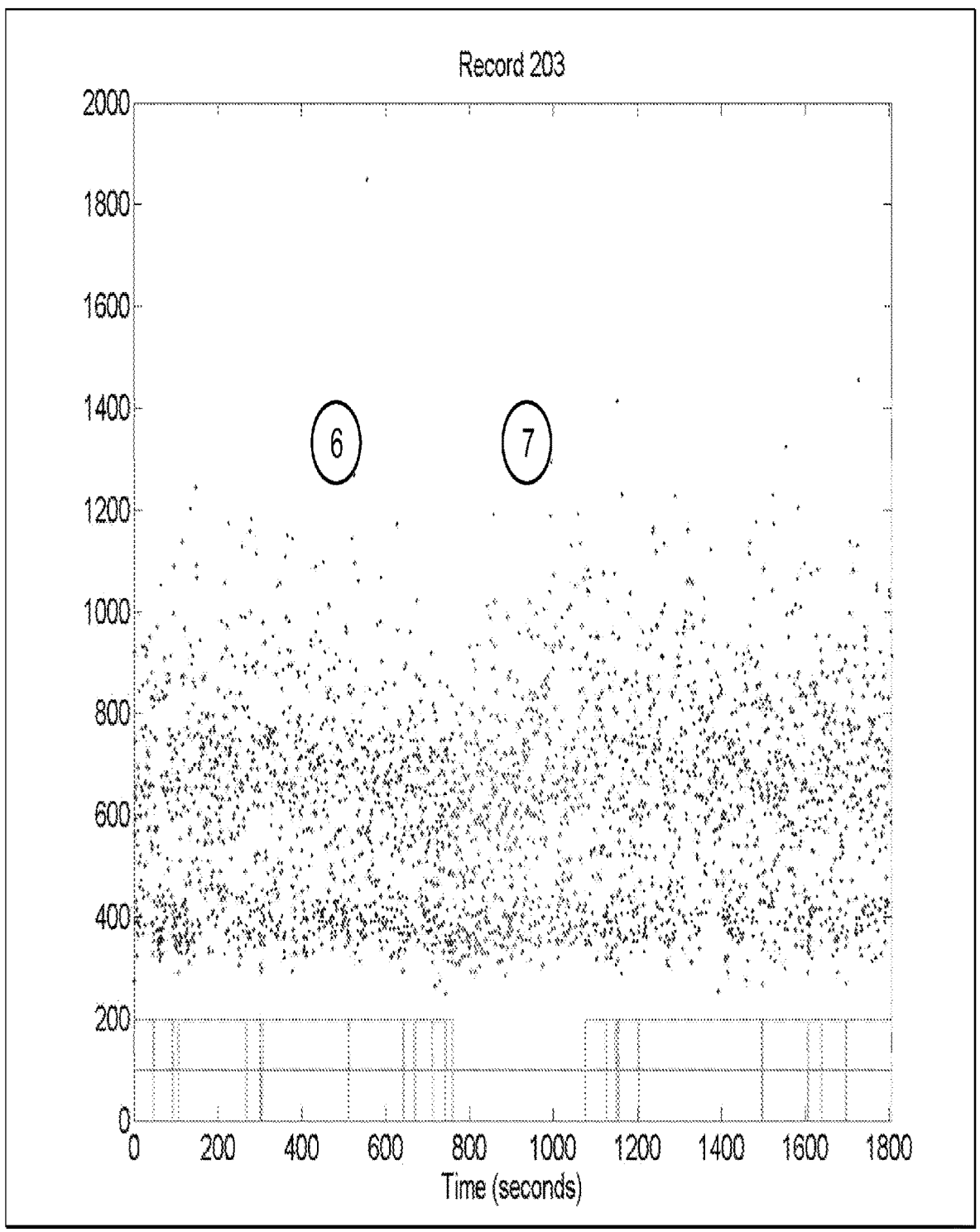
FIG. 12 shows a complete 30 minute RR interval time series from Record 203 in Table 4.
Figure 13:
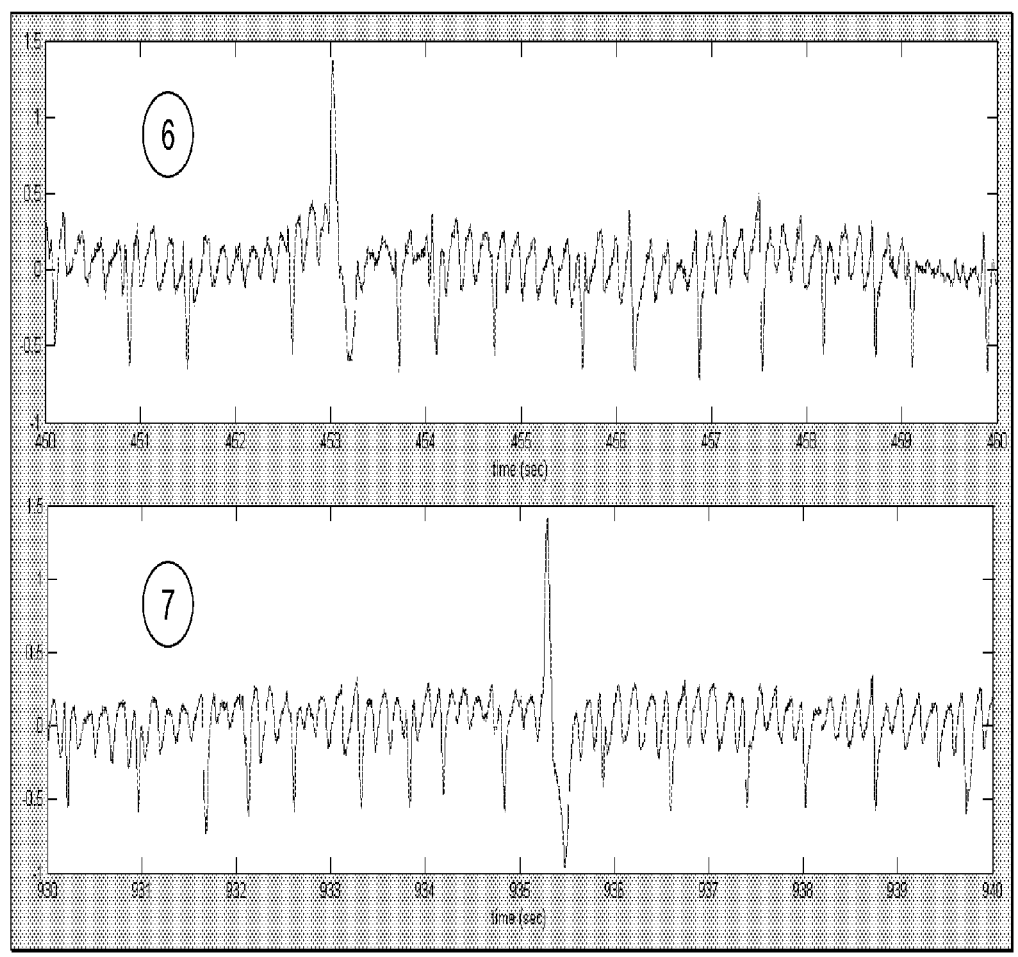
FIG. 13 shows EKG strips from labeled areas of FIG. 12.

FIG. 12 shows the entire 30 minute RR interval time series for Record 203. There is no obvious change in rhythm, and we detect AF throughout. The electrocardiographer found the section in the middle to be atrial flutter and the rest to be AF. In FIG. 13, strips 6 and 7 show, to our eye, identical rhythm that we would characterize as somewhat organized AF with either PVCs or aberrantly conducted impulses. We see no reason to call them different rhythms.

The conclusion is that the labeling of rhythm in the ARH database is open, in some places, for discussion. A detection algorithm that correctly follows all of the ARH labeling is, in our opinion, overfit.

A first limitation for arrhythmias other than AF is recognized. False negatives are expected in atrial flutter and AF with a more organized atrial activation—these are more regular rhythms and resistant to diagnosis by changes in entropy. This problem is recognized in the epicmp analysis, which excludes atrial flutter episodes from evaluation of AF detection. False positives are expected in frequent ectopy, atrial or ventricular—these are irregular rhythms for the most part, and will have higher entropy. A second limitation is recognized with regard to arbitrary use of 30 seconds as a minimum length of AF. This is untested from a clinical point of view, and it is possible that even these short episodes increase stroke risk. This problem is shared by all AF detection strategies.

Example 6—AF Detection Using COSEn in the UVa Holter Database

This example focuses on the UVa Holter database. More specifically, this example examines COSEn distributions in consecutive patients. More than 600 consecutive 24-hour Holter recordings, including digitized waveforms, RR intervals and rhythm labels from the Philips system are available. Furthermore, this example inspects of the EKG waveforms to verify the rhythm labeling in records of patients over 45 years of age in whom atrial fibrillation (AF) was detected. In addition, this example involves inspection of the first 100 consecutive records.

Figure 14:
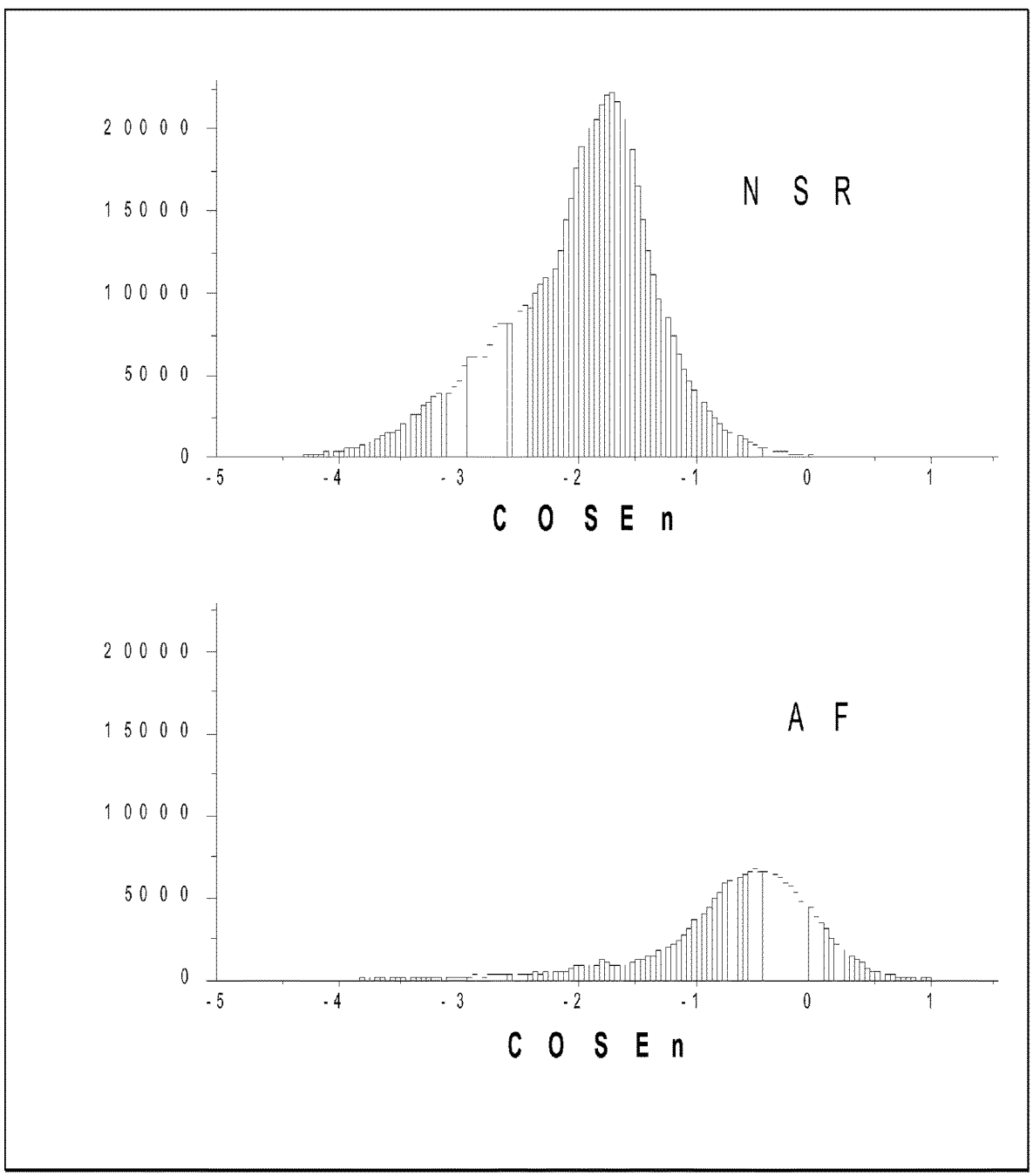
FIG. 14 shows histograms of COSEn of more than 700,000 16-beat segments from 114 24-hour records for which the rhythm labels of normal sinus rhythm (NSR) or AF were corrected.

First, regarding AF detection using COSEn in the UVa Holter database, FIG. 14 shows histograms of COSEn of more than 700,000 16-beat segments from 114 24-hour records for which the rhythm labels of normal sinus rhythm (NSR) or AF have been corrected. There is reasonable separation, and a cut-off value of −1 is suggested from inspection. Note that there is a little hump in the tail to the left in the histogram of COSEn in AF, centered on COSEn values around −2, indicating a more regular set of RR intervals than the rest of the group. These data have been identified and the corresponding EKG will be inspected more closely. Because of record selection, AF is over-represented in these histograms. Overall, about 10% of the data set seems to be AF.

We have characterized the rhythms as AF or not, based on (1) COSEn calculation of 16-beat segments and (2) near-real time segmentation, and compared the results to our labeling from EKG inspection. The results in epicmp and sumstats format for the 22 patients over age 45 (of more than 70 total) that have been inspected with at least some detected AF are presented in Table 6.

duration of AF episodes by EKG inspection in green, and as detected by COSEn in purple.

Figure 16:
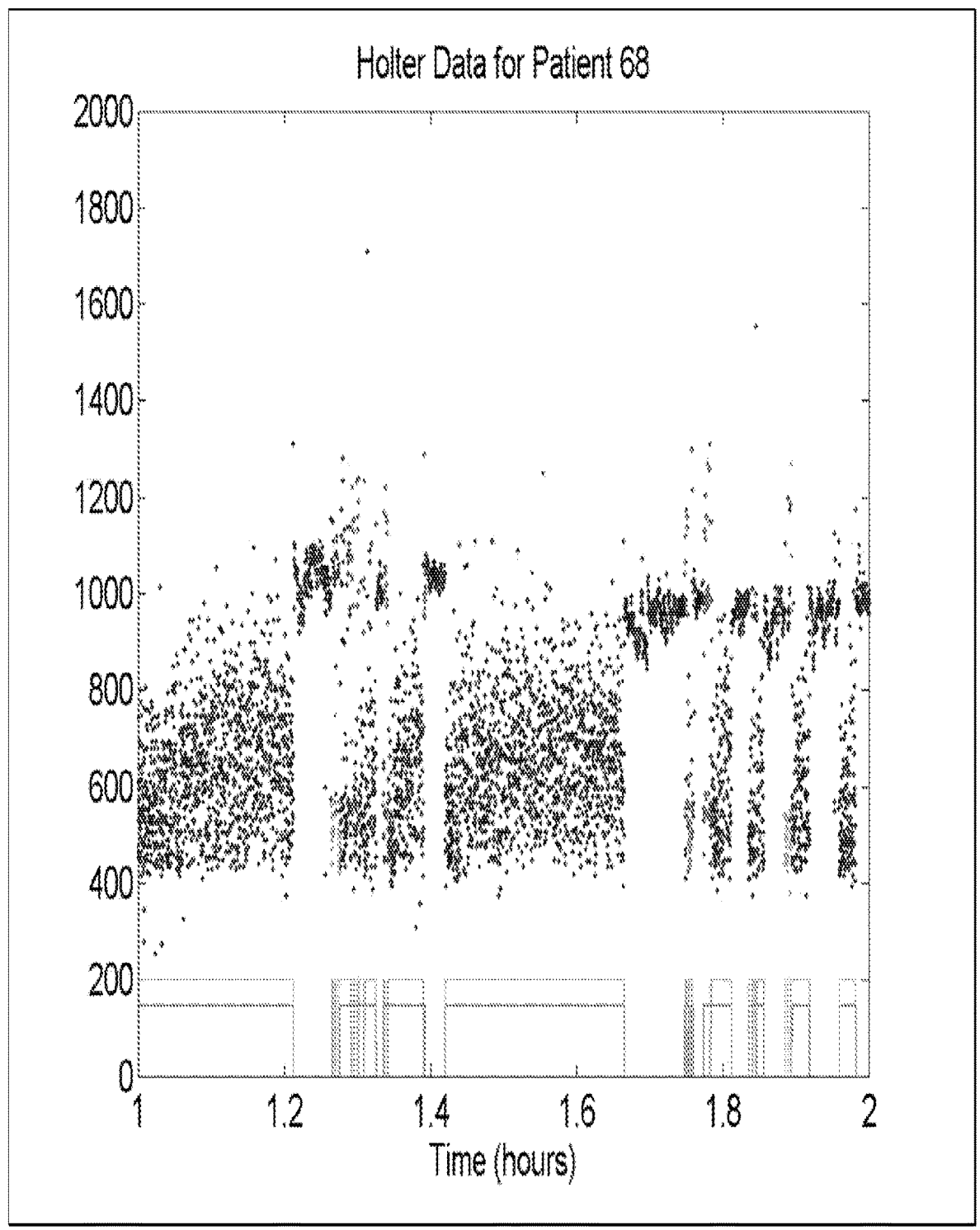
FIG. 16 shows hour 2 of the 24 hour RR interval data and rhythm analysis shown in FIGS.

Examination of FIG. 16, by eye, demonstrates that the agreement is good. Thus the major findings are that COSEn detects AF, and the segmentation assigns onsets and offsets accurately.

Example 7—Histograms of COSEn in the MIT and UVa Databases

Figure 17:
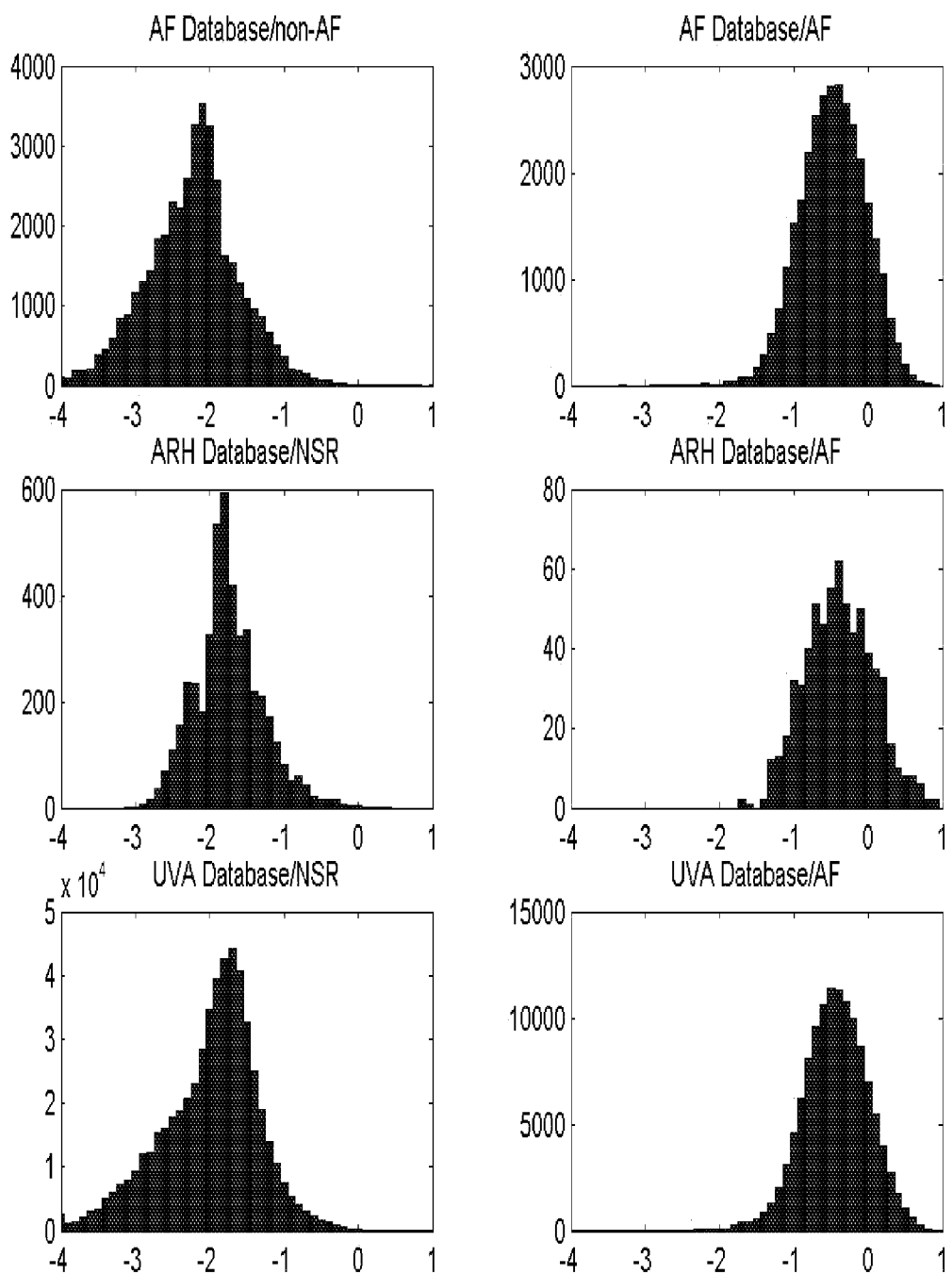
FIG. 17 shows histograms of COSEn calculated in 16-beat segments from the entire MIT AF (top panels) and ARH (middle panels) databases and from the more than 100 UVa Holter recordings that we have over read (bottom panels). The left-hand panels are all rhythms other than AF, and the right-hand panels are AF alone.

FIG. 17 shows histograms of COSEn calculated in 16-beat segments from the entire MIT AF (top panels) and ARH (middle panels) databases and from the more than 100 UVa Holter recordings that we have overread (bottom panels). The left-hand panels are all rhythms other than AF, and the right-hand panels are AF alone. The findings are of

TABLE 6

| Record | TPs | FN | TPp | FP | ESe | E + P | DSe | D + P | Ref duration | Test duration |
|---|---|---|---|---|---|---|---|---|---|---|
| 11 | 4 | 0 | 13 | 0 | 100 | 100 | 98 | 100 | 23:59:37.480 | 23:32:58.885 |
| 27 | 2 | 0 | 23 | 0 | 100 | 100 | 99 | 100 | 23:59:09.230 | 23:38:47.165 |
| 30 | 0 | 0 | 0 | 0 | — | — | — | — | 0.000 | 0.000 |
| 38 | 4 | 0 | 9 | 0 | 100 | 100 | 99 | 100 | 23:56:11.465 | 23:45:47.130 |
| 62 | 1 | 0 | 8 | 0 | 100 | 100 | 100 | 100 | 23:59:13.065 | 23:52:55.730 |
| 67 | 1 | 0 | 73 | 0 | 100 | 100 | 45 | 100 | 22:46:29.785 | 10:09:50.740 |
| 68 | 52 | 3 | 50 | 4 | 95 | 93 | 99 | 98 | 13:37:41.115 | 13:45:55.700 |
| 74 | 2 | 0 | 3 | 0 | 100 | 100 | 100 | 100 | 23:58:23.050 | 23:58:39.525 |
| 87 | 1 | 0 | 1 | 0 | 100 | 100 | 100 | 100 | 23:59:49.880 | 23:59:49.880 |
| 137 | 4 | 0 | 1 | 0 | 100 | 100 | 100 | 100 | 23:59:40.085 | 23:59:49.680 |
| 141 | 2 | 0 | 52 | 0 | 100 | 100 | 98 | 98 | 23:35:58.685 | 23:25:20.400 |
| 144 | 1 | 0 | 1 | 0 | 100 | 100 | 100 | 100 | 23:59:50.010 | 23:59:50.010 |
| 147 | 1 | 0 | 74 | 0 | 100 | 100 | 95 | 100 | 23:59:50.045 | 22:43:55.675 |
| 153 | 1 | 0 | 1 | 0 | 100 | 100 | 100 | 100 | 23:59:50.185 | 23:59:50.185 |
| 154 | 3 | 0 | 11 | 1 | 100 | 92 | 94 | 97 | 3:55:35.235 | 3:50:10.340 |
| 250 | 3 | 0 | 154 | 0 | 100 | 100 | 59 | 100 | 23:59:39.715 | 14:13:52.625 |
| 282 | 2 | 0 | 2 | 5 | 100 | 29 | 99 | 94 | 1:26:52.315 | 1:31:34.550 |
| 296 | 1 | 0 | 15 | 0 | 100 | 100 | 99 | 100 | 23:59:50.105 | 23:47:48.675 |
| 387 | 1 | 0 | 5 | 0 | 100 | 100 | 100 | 100 | 23:59:50.105 | 23:59:09.835 |
| 391 | 2 | 0 | 24 | 66 | 100 | 27 | 42 | 47 | 3:03:06.560 | 2:41:43.370 |
| 1088 | 16 | 0 | 7 | 0 | 100 | 100 | 100 | 100 | 23:58:46.520 | 23:54:19.710 |
| 1090 | 2 | 0 | 9 | 0 | 100 | 100 | 100 | 100 | 23:59:47.405 | 23:57:09.450 |
| Sum | 106 | 3 | 536 | 76 | | | | | 428:15:12.040 | 402:49:19.260 |
| Gross | | | | | 97 | 88 | 94 | 100 | | |
| Average | | | | | 100 | 92 | 92 | 97 | | |

Summary of results from 22 records

By inspection of consecutive records, circumstances can be identified in which false positive and negative findings of AF occur. False positives (high entropy not due to AF) occur in circumstances of very frequent PVCs or PACs; very high heart rate variability in the young; SA Wenckebach; and/or multifocal atrial tachycardia. False negative readings of AF (low entropy despite AF) occur in circumstances of atrial flutter or organized AF with regular ventricular response (recall that epicmp excludes atrial flutter from its analysis); and/or very slow heart rates.

As an example of the potential capability of the algorithm, results for a Holter showing paroxysmal AF are presented. In this small data set, this was the only record with false negative findings using COSEn.

Figure 15:
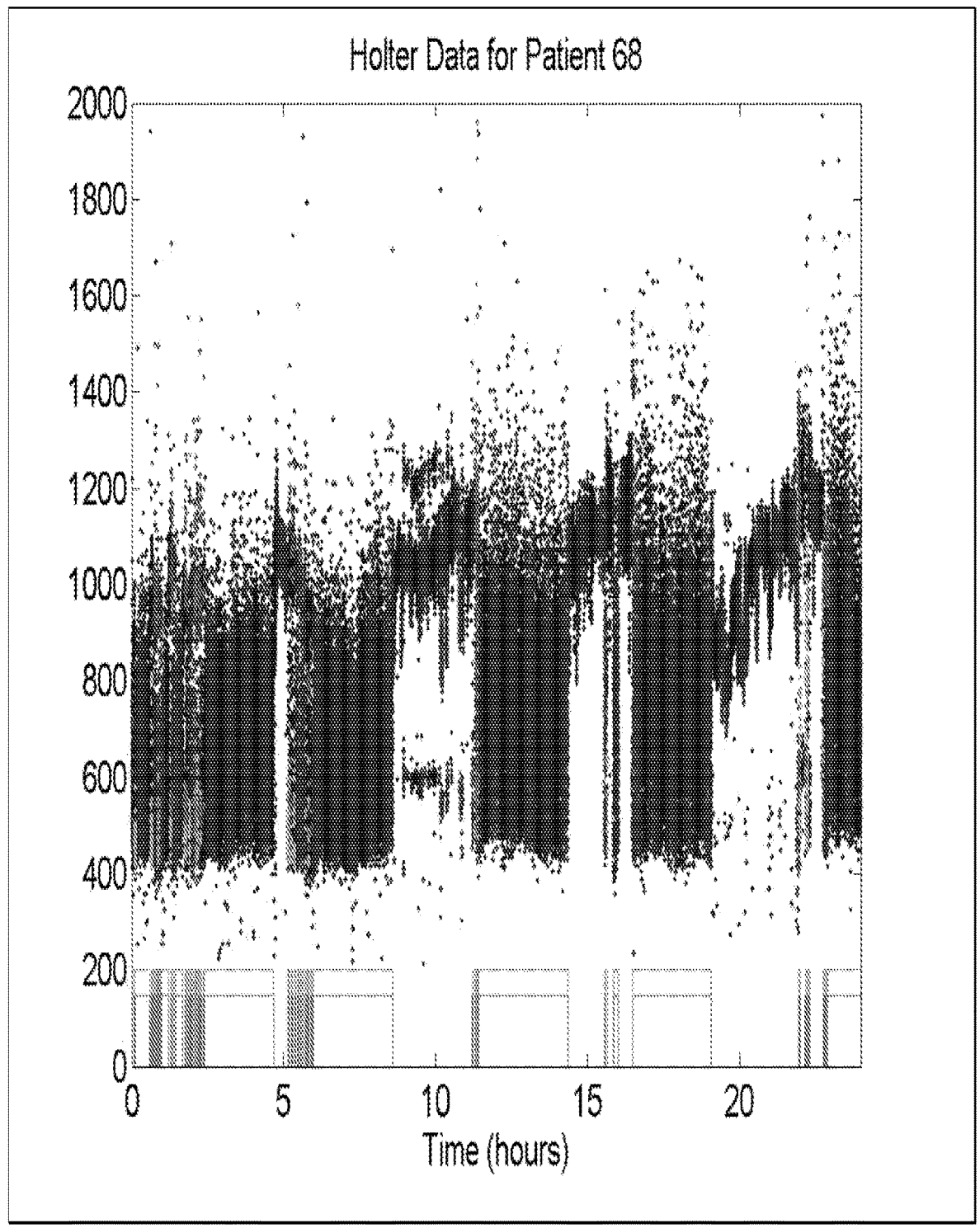
FIG. 15 shows 24 hour RR interval data and rhythm analysis. AF is marked by open green bars (rhythm labeling from EKG inspection) and open purple bars (COSEn analysis).

FIG. 15 and FIG. 16 show the RR interval time series as points, and the AF episode durations as open bars below. FIG. 15 is the entire 24 hours, and FIG. 16 is the second hour of the recording. In these figures, blue points are RR intervals for which COSEn agrees with our own interpretation of the EKG, whether NSR or AF; red points are intervals that COSEn labeled as AF but were not AF by EKG inspection; green points are AF intervals by EKG inspection that COSEn did not label as AF; and open bars show higher COSEn in AF, with similar properties in the MIT and UVa databases. Note the labeling of the y-axes—the UVa database has more than 100 times as much AF as the MIT ARH database, and is growing.

The histogram of COSEn in AF at UVa, presented in FIG. 17, differs from the one showed in Example 6. The "small tail" to which attention was drawn in Example 6, arose from a single patient. The RR interval time series of that record showed long segments of very regular rhythm, but no atrial activity was seen in the 3 EKG leads from the Holter recording. A 12-lead EKG from that day, though, showed unmistakable atrial activity that was either atrial flutter or atrial tachycardia but was not AF. This record (like all the records with atrial flutter) was removed from the AF set, which now numbers 29.

These findings suggest that the UVa database should be an acceptable test bed for arrhythmia detection algorithms, and a candidate as a surrogate for the MIT databases for FDA approval.

Table 7 presents epicmp and sumstats for 29 UVa Holter recordings.

TABLE 7

| Record | TPs | FN | TPp | FP | ESe | E + P | DSe | D + P | Ref duration | Test duration |
|---|---|---|---|---|---|---|---|---|---|---|
| 11 | 4 | 0 | 13 | 0 | 100 | 100 | 98 | 100 | 23:59:37.480 | 23:32:58.885 |
| 27 | 2 | 0 | 23 | 0 | 100 | 100 | 99 | 100 | 23:59:09.230 | 23:38:47.165 |
| 30 | 0 | 0 | 0 | 0 | — | — | — | — | 0.000 | 0.000 |
| 38 | 4 | 0 | 9 | 0 | 100 | 100 | 99 | 100 | 23:56:11.465 | 23:45:47.130 |
| 62 | 1 | 0 | 8 | 0 | 100 | 100 | 100 | 100 | 23:59:13.065 | 23:52:55.730 |
| 67 | 1 | 0 | 73 | 0 | 100 | 100 | 45 | 100 | 22:46:29.785 | 10:09:50.740 |
| 68 | 52 | 3 | 50 | 4 | 95 | 93 | 99 | 98 | 13:37:41.115 | 13:45:55.700 |
| 74 | 2 | 0 | 3 | 0 | 100 | 100 | 100 | 100 | 23:58:23.050 | 23:58:39.525 |
| 87 | 1 | 0 | 1 | 0 | 100 | 100 | 100 | 100 | 23:59:49.880 | 23:59:49.880 |
| 137 | 4 | 0 | 1 | 0 | 100 | 100 | 100 | 100 | 23:59:40.085 | 23:59:49.680 |
| 141 | 2 | 0 | 52 | 0 | 100 | 100 | 98 | 98 | 23:35:58.685 | 23:25:20.400 |
| 144 | 1 | 0 | 1 | 0 | 100 | 100 | 100 | 100 | 23:59:50.010 | 23:59:50.010 |
| 147 | 1 | 0 | 74 | 0 | 100 | 100 | 95 | 100 | 23:59:50.045 | 22:43:55.675 |
| 153 | 1 | 0 | 1 | 0 | 100 | 100 | 100 | 100 | 23:59:50.185 | 23:59:50.185 |
| 154 | 3 | 0 | 11 | 1 | 100 | 92 | 94 | 97 | 3:55:35.235 | 3:50:10.340 |
| 177 | 31 | 0 | 16 | 1 | 100 | 94 | 100 | 99 | 23:37:03.840 | 23:47:52.565 |
| 190 | 1 | 0 | 1 | 0 | 100 | 100 | 100 | 90 | 0:52.075 | 0:57.835 |
| 194 | 4 | 0 | 3 | 0 | 100 | 100 | 100 | 100 | 23:51:00.810 | 23:50:56.540 |
| 200 | 2 | 0 | 4 | 0 | 100 | 100 | 100 | 100 | 23:59:48.455 | 23:58:19.810 |
| 205 | 6 | 0 | 8 | 0 | 100 | 100 | 99 | 100 | 23:59:16.540 | 23:44:41.935 |
| 245 | 10 | 0 | 4 | 0 | 100 | 100 | 100 | 100 | 23:59:12.045 | 23:58:36.975 |
| 252 | 136 | 0 | 10 | 0 | 100 | 100 | 100 | 98 | 23:32:00.440 | 23:54:58.890 |
| 282 | 2 | 0 | 2 | 5 | 100 | 29 | 99 | 94 | 1:26:52.315 | 1:31:34.550 |
| 291 | 2 | 0 | 1 | 0 | 100 | 100 | 100 | 100 | 23:59:45.040 | 23:59:50.195 |
| 296 | 1 | 0 | 15 | 0 | 100 | 100 | 99 | 100 | 23:59:50.105 | 23:47:48.675 |
| 384 | 4 | 0 | 3 | 63 | 100 | 5 | 100 | 28 | 2:49:00.090 | 10:04:12.690 |
| 387 | 1 | 0 | 5 | 0 | 100 | 100 | 100 | 100 | 23:59:50.105 | 23:59:09.835 |
| 1088 | 16 | 0 | 7 | 0 | 100 | 100 | 100 | 100 | 23:58:46.520 | 23:54:19.710 |
| 1090 | 2 | 0 | 9 | 0 | 100 | 100 | 100 | 100 | 23:59:47.405 | 23:57:09.450 |
| Sum | 297 | 3 | 408 | 74 | | | | | 571:00:25.100 | 563:14:10.700 |
| Gross | | | | | 99 | 85 | 97 | 99 | | |
| Average | | | | | 100 | 93 | 97 | 97 | | |

Summary of results from 29 records

Note that in Table 7, about 95% of the data is AF. Note also that record 384 has a large number of false positives. The EKG shows very frequent atrial ectopy and a very variable rhythm, but nonetheless is not AF.

The finding is that COSEn measurements of 16-beat segments and implementing a near-real time segmentation algorithm has excellent performance in detecting AF in patients who are evaluated for that diagnosis.

The following references are hereby incorporated by reference herein in their entirety:

[1] K. Tateno and L. Glass, "Automatic detection of atrial fibrillation using the coefficient of variation and density histograms of RR and ΔRR intervals," Med Biol Eng Comput vol. 39, 664-671, 2001.

[2] S. Pincus, "Approximate entropy as a measure of system complexity," Proc. Natl. Acad. Sci., vol. 88, pp. 2297-2301, 1991.

[3] J. Richman and J. Moorman, "Physiological time series analysis using approximate entropy and sample entropy," Amer J Physiol, vol. 278, pp. H2039-H2049, 2000.

[4] D. Lake, J. Richman, M. Griffin, and J. Moorman, "Sample entropy analysis of neonatal heart rate variability," Amer J Physiol, vol. 283, pp. R789-R797, 2002.

[5] M. Costa, A. Goldberger, and C. Peng, "Multiscale entropy analysis of complex physiologic time series," Phys. Rev. Lett., vol. 89, no. 6, p. 068102, 2002.

[6] J. Beirlant, E. J. Dudewicz, L. Gyorfi, and E. C. van der Meulen, "Nonparametric entropy estimation: An overview," International Journal of Math. Stat. Sci., vol. 6, no. 1, pp. 17-39, 1997.

[7] O. Vasicek, "A test for normality based on sample entropy," Journal of the Royal Statistical Society, Series B, vol. 38, no. 1, pp. 54-59, 1976.

[8] A. Hyvarinen, J. Karhunen, and E. Oja, Independent Component Analysis. John Wiley and Sons, 2001.

[9] M. Jones and R. Sibson, "What is projection pursuit?" Journal of the Royal Statistical Society, Series A, vol. 150, pp. 1-36, 1987.

[10] B. Ripley, Pattern recognition and neural networks. Cambridge University Press, 1996.

[11] L. Breiman, J. Friedman, R. Olshen, and C. Stone, Classification and Regression Trees. Monterey, Calif.: Wandsworth and Brooks-Cole, 1984.

[12] R. T. and C. N., Goodness-of-Fit Statistics for Discrete Multivariate Data. New York: Springer-Verlag, 1988.

[13] C. E. Shannon, "A Mathematical Theory of Communication", Bell System Technical Journal, vol. 27, pp. 379-423 & 623-656, July & October, 1948

[14] H. Kantz and T. Schreiber, Nonlinear Time Series Analysis. Cambridge: Cambridge University Press, 1997.

[15] P. Brockwell and A. Davis, Time Series: Theory and Methods. Springer, 1991.

[16] J. Richman, "Sample entropy statistics," Ph.D. dissertation, University of Alabama Birmingham, 2004.

[17] B. L. S. P. Rao, Nonparametric Functional Estimation. London: Academic Press, Inc., 1983.

[18] D. Erdogmus, K. Hild, J. Principe, M. Lazaro, and I. Santamaria, "Adaptive blind deconvolution of linear channels using Renyi's entropy with Parzen window estimation," IEEE Transactions on Signal Processing, vol. 52, no. 6, pp. 1489-1498, 2004.

[19] Lake D E, Renyi entropy measures of heart rate Gaussianity. IEEE Transactions on Biomedical Engineering, Volume 53(1):21-27, 2006.

[20] Lake D E. Efficient adaptive signal and signal dimension estimation using piecewise projection libraries Wavelet Applications V, H. H. Szu, Editor, Proc. SPIE Vol. 3391, p. 388-395, 1998.

[21] Lake D E. Adaptive signal estimation using projection libraries (Invited Paper) Wavelet Applications IV, H. H. Szu, Editor, Proc. SPIE-3078, p.p. 602-609, 1997.

The following Patents, Applications and Publications are hereby incorporated by reference herein in their entirety:

U.S. Patent Publication No. 2005/0004486A1 to Glass et al., entitled "Detection of Cardiac Arrhythmia Using Mathematical Representation of Standard Deltarr Probability Density Histograms;"

U.S. Patent Publication No. 2005/0165320A1 to Glass et al., entitled "Method and System for Detection of Cardiac Arrhythmia;"

International Patent Publication No. WO 03/077755A1 to Tateno et al., entitled "Detection of Cardiac Arrhythmia Using Mathematical Representation of Standard $\Delta rr$ Probability Density Histograms;"

International Patent Publication No. WO 02/24068A1 to Glass et al., entitled "Method and System for Detection of Cardiac Arrhythmia;"

European Patent No. EP1485018 to Tateno et al., entitled "Detection of Cardiac Arrhythmia Using Mathematical Representation of Standard DRR Probability Density Histograms;" and European Patent Publication No. EP1322223A1 to Glass et al., entitle "(ENG) Method and System for Detection of Cardiac Arrhythmia."

The invention claimed is:

1. A method for analyzing at least one cardiac rhythm, wherein the method employs multivariate statistical models that employ entropy measures, wherein the at least one cardiac rhythm comprises an RR-interval series, and wherein the method comprises characterizing RR intervals by at least one dynamic parameter;
   combining the at least one dynamic parameter with at least one density parameter;
   classifying the at least one cardiac rhythm based on the combination of the at least one dynamic parameter and the at least one density parameter; and
generating a diagnostic output based on the classification.

2. The method of claim 1, wherein the at least one dynamic parameter is selected from the group consisting of differential quadratic Renyi entropy rate measured using the SampEn algorithm, normalized sample entropy (SE), non-normalized sample entropy (Q), and the coefficient of sample entropy (COSEn).

3. The method of claim 2, wherein the at least one density parameter is selected from the group consisting of standard deviation and coefficient of variation (CV) measured using histogram summary statistics.

4. The method of claim 2, wherein the characterization of RR-intervals by the at least one dynamic parameter takes into account the order of data points in the RR-interval series.

5. The method of claim 2, wherein the at least one density parameter is considered as a continuous value, not as a range.

6. The method of claim 2, further comprising optimizing the accuracy and discriminating capability of the entropy measures by applying a continuity correction.

7. The method of claim 2, further comprising estimating the standard error of sample entropy and COSEn.

8. The method of claim 2, furthering comprising a first step of identifying at least one segment of the at least one cardiac rhythm, wherein the RR interval distribution of the at least one segment displays statistical homogeneity.

9. The method of claim 8, wherein the statistical homogeneity is measured in terms of the mean, and/or the standard deviation of the RR interval distribution.

10. An apparatus comprising a programmable computer controller, programmed to: analyze at least one cardiac rhythm, comprising an RR interval series by characterizing RR intervals by at least one dynamic parameter; combine the at least one dynamic parameter with at least one density parameter; and classify the at least one cardiac rhythm based on the combination of the at least one dynamic parameter and the at least one density parameter.

* * * * *